(12) United States Patent
Renna et al.

(10) Patent No.: US 8,101,448 B2
(45) Date of Patent: Jan. 24, 2012

(54) MANUFACTURING METHOD OF A GAS SENSOR INTEGRATED ON A SEMICONDUCTOR SUBSTRATE

(75) Inventors: Crocifisso Marco Antonio Renna, Gela (IT); Alessandro Auditore, Giarre (IT); Alessio Romano, Catania (IT); Sebastiano Ravesi, Sant'Agata Li Battiati (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 141 days.

(21) Appl. No.: 12/413,346

(22) Filed: Mar. 27, 2009

(65) Prior Publication Data

US 2009/0243003 A1 Oct. 1, 2009

(30) Foreign Application Priority Data

Mar. 28, 2008 (IT) .................... MI08A0532

(51) Int. Cl.
*H01L 21/00* (2006.01)

(52) U.S. Cl. .................. 438/49; 438/422; 257/E21.573; 73/31.06

(58) Field of Classification Search ............. 438/48, 438/382, 411, 421, 422, 652, 49; 257/414, 257/622, E21.004, E21.573, E29.166; 73/25.05, 73/31.06; 204/424, 431
See application file for complete search history.

(56) References Cited

U.S. PATENT DOCUMENTS

| | | | |
|---|---|---|---|
| 6,329,696 B1* | 12/2001 | Tanaka | 257/419 |
| 6,906,392 B2* | 6/2005 | Benzel et al. | 257/414 |
| 7,193,256 B2 | 3/2007 | Renna et al. | |
| 7,235,456 B2* | 6/2007 | Sato et al. | 438/411 |
| 2002/0063365 A1* | 5/2002 | Vigliotti et al. | 264/618 |
| 2002/0142478 A1* | 10/2002 | Wado et al. | 436/151 |
| 2003/0042627 A1* | 3/2003 | Farrar et al. | 257/797 |
| 2003/0168711 A1* | 9/2003 | Villa et al. | 257/506 |
| 2004/0248349 A1* | 12/2004 | Renna et al. | 438/197 |
| 2005/0229379 A1* | 10/2005 | Totokawa | 29/592.1 |
| 2007/0057355 A1* | 3/2007 | Barlocchi et al. | 257/678 |
| 2007/0062812 A1* | 3/2007 | Weber et al. | 204/431 |
| 2008/0029817 A1* | 2/2008 | Barlocchi et al. | 257/350 |
| 2008/0044939 A1* | 2/2008 | Nassiopoulou et al. | 438/54 |
| 2008/0134753 A1* | 6/2008 | Jun et al. | 73/23.2 |
| 2009/0151429 A1* | 6/2009 | Jun et al. | 73/31.06 |
| 2010/0147685 A1* | 6/2010 | Ikawa et al. | 204/431 |

FOREIGN PATENT DOCUMENTS

JP 2003215095 A * 7/2003

* cited by examiner

*Primary Examiner* — Matthew Landau
*Assistant Examiner* — Joseph C Nicely
(74) *Attorney, Agent, or Firm* — Lisa K. Jorgenson; Robert Iannucci; Seed IP Law Group PLLC

(57) ABSTRACT

A method manufactures a gas sensor integrated on a semiconductor substrate. The method includes: realizing a first plurality of openings in the semiconductor substrate; realizing a crystalline silicon membrane suspended on the semiconductor substrate, forming an insulating cavity buried in the substrate; realizing a second plurality of openings in the semiconductor substrate, so as to totally suspend on the semiconductor substrate the crystalline silicon membrane; realizing, through a thermal oxidation process of the totally suspended crystalline silicon membrane, a suspended dielectric membrane; realizing, through selective photolithography, a heating element; realizing, through selective photolithography, electrodes and a pair of electric contacts; and selectively realizing, above the electrodes, a sensitive element by compacting layers of metallic oxide through a sintering process generated in the gas sensor by connecting the electrodes to a voltage generator.

19 Claims, 33 Drawing Sheets

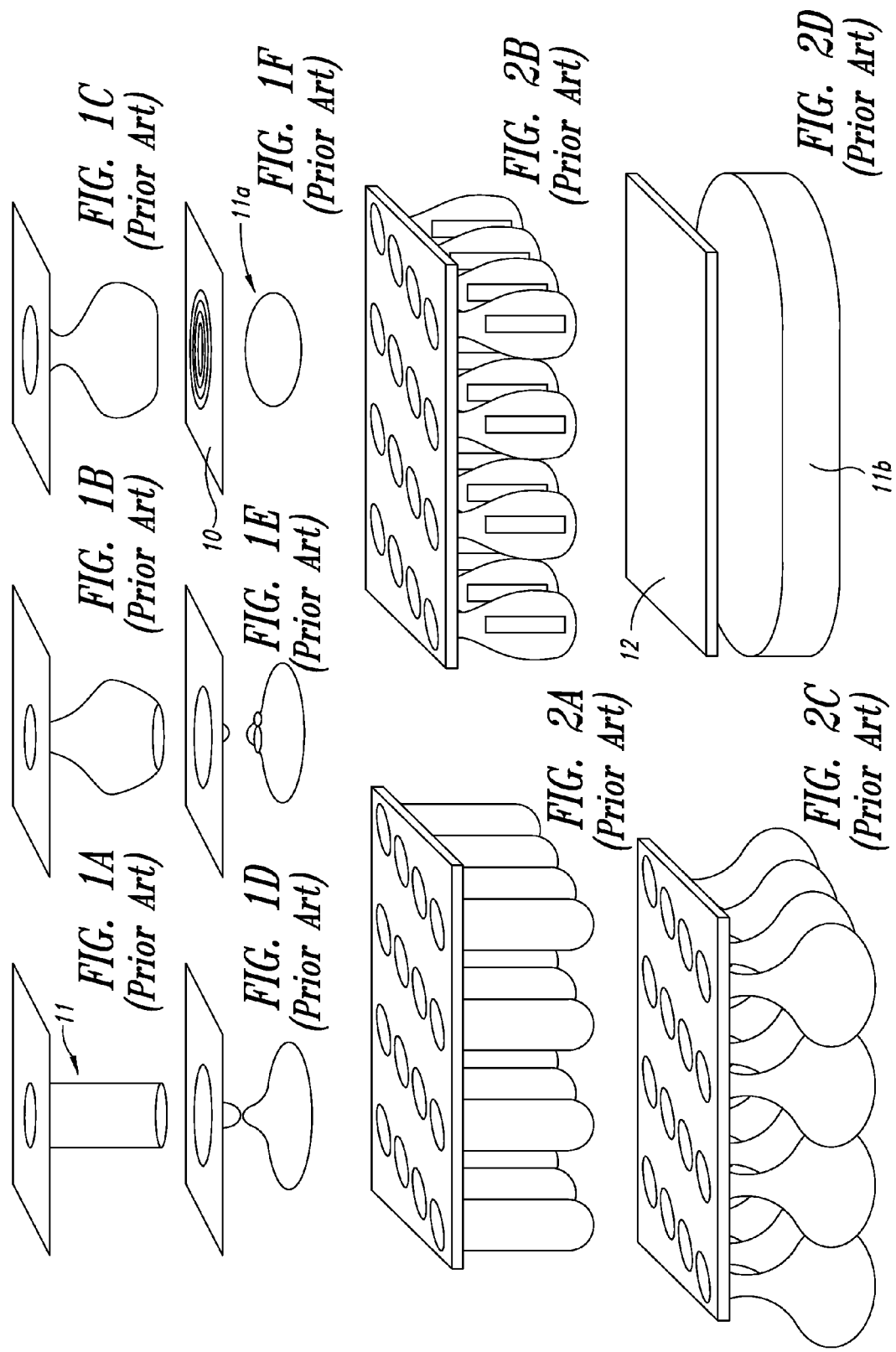

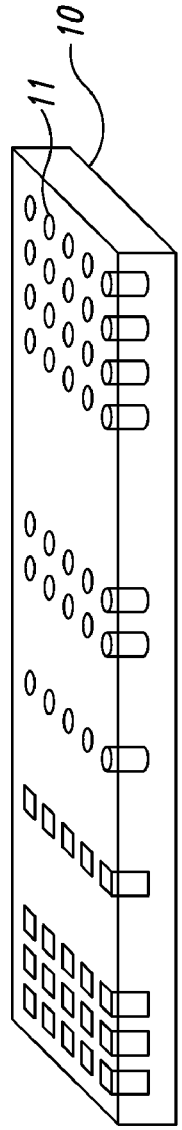
FIG. 3
(Prior Art)
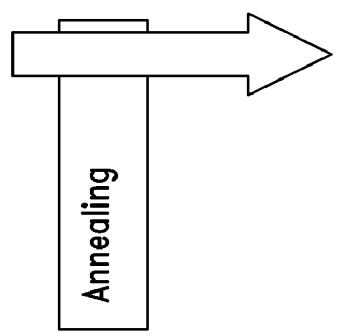
Annealing
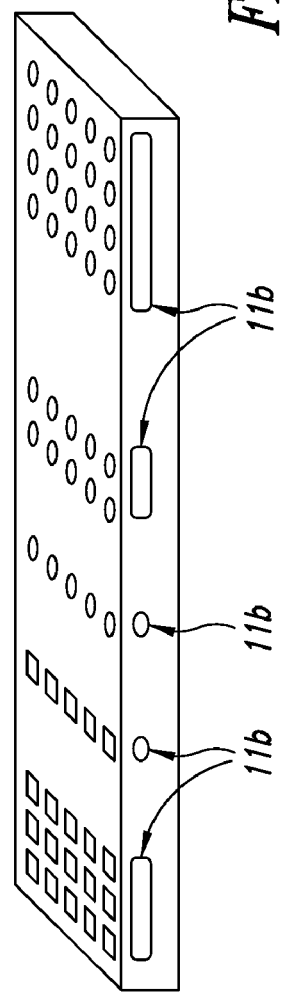
FIG. 4
(Prior Art)

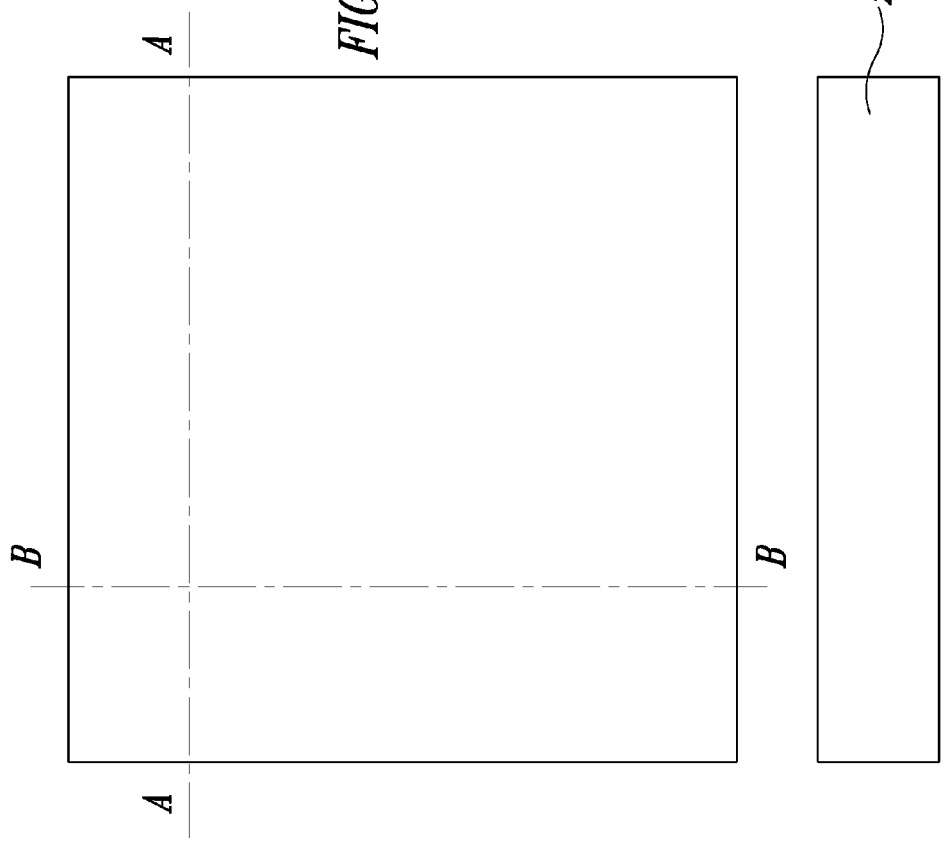

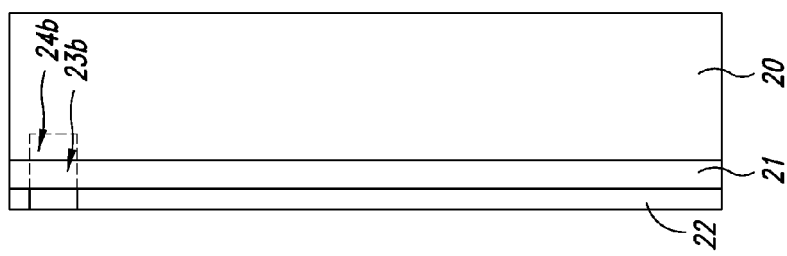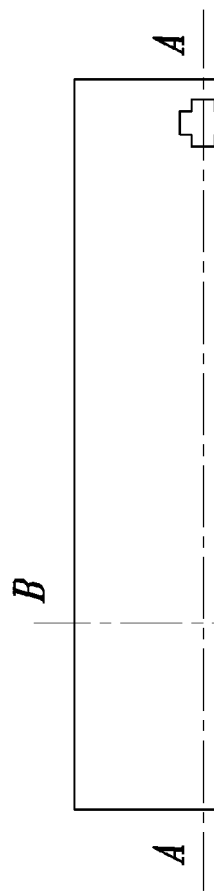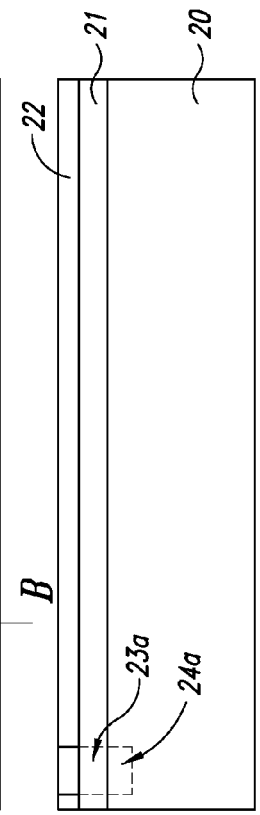
FIG. 7A
FIG. 7B
FIG. 7C

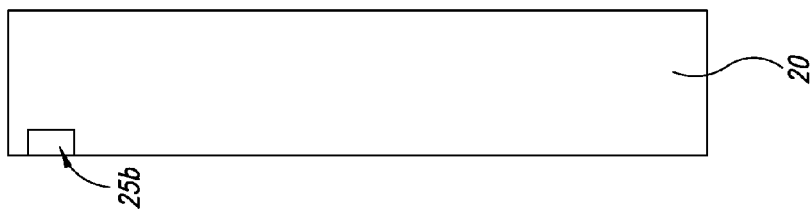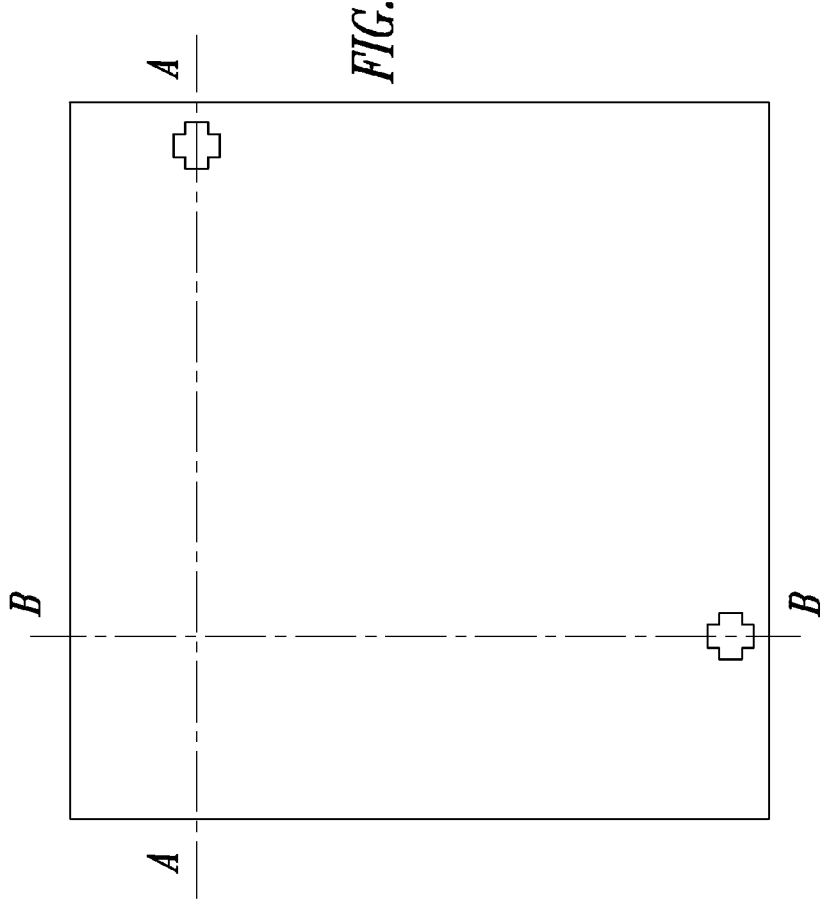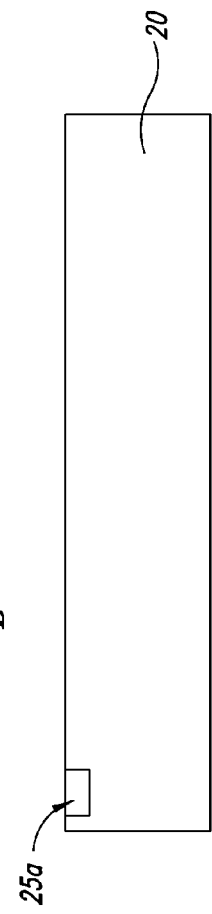

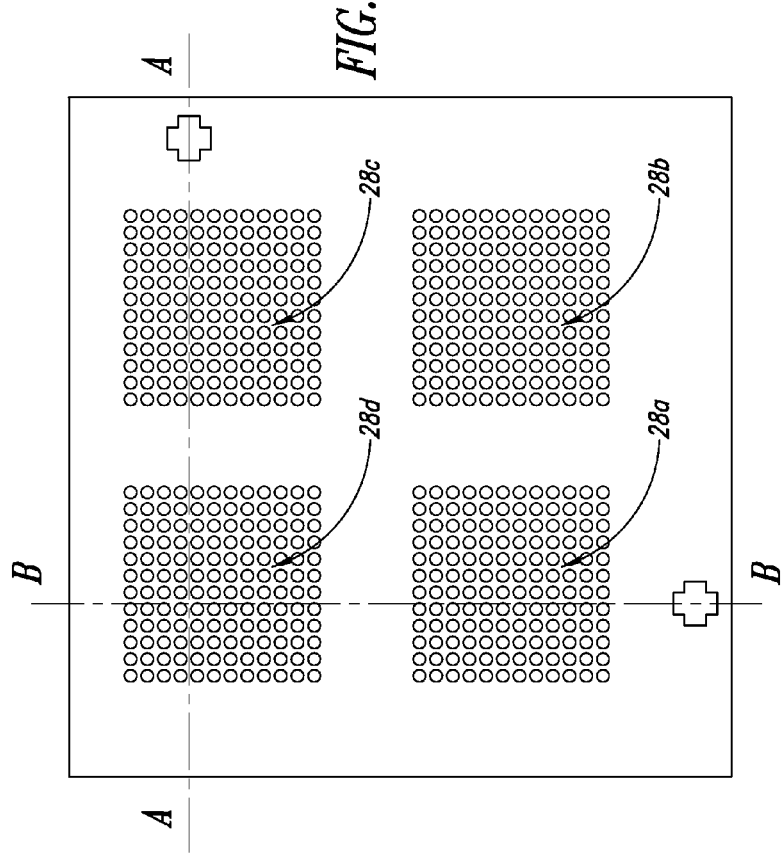
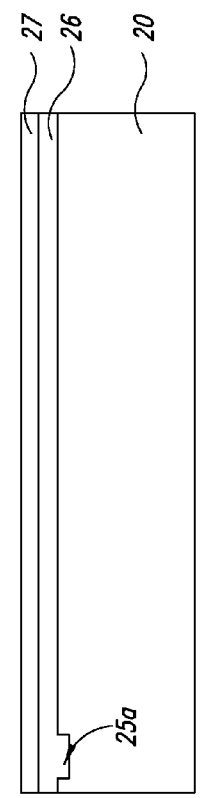
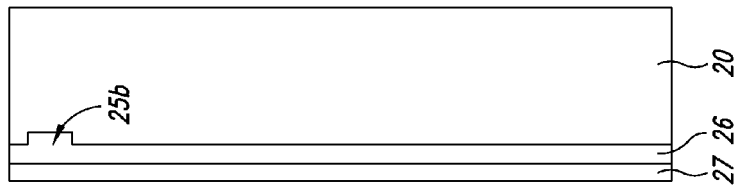
FIG. 11A
FIG. 11B
FIG. 11C

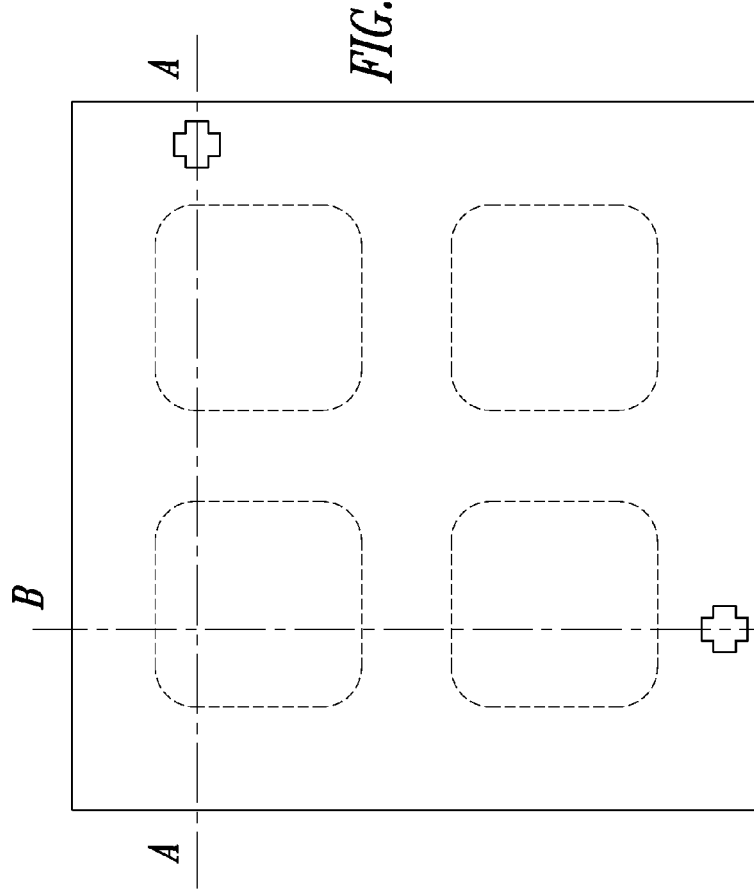
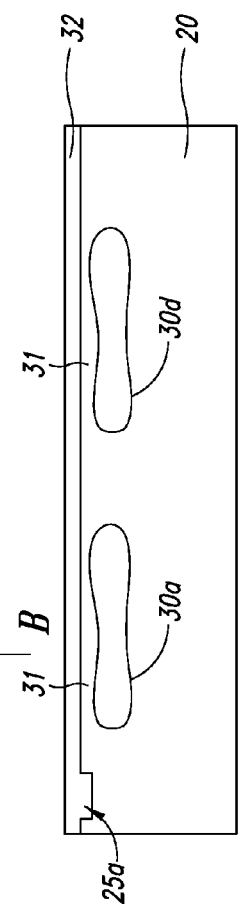
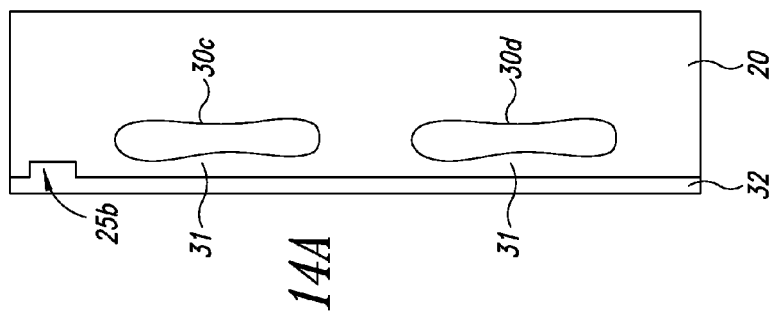

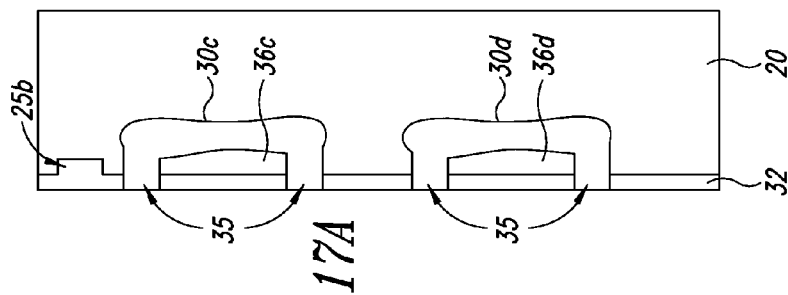
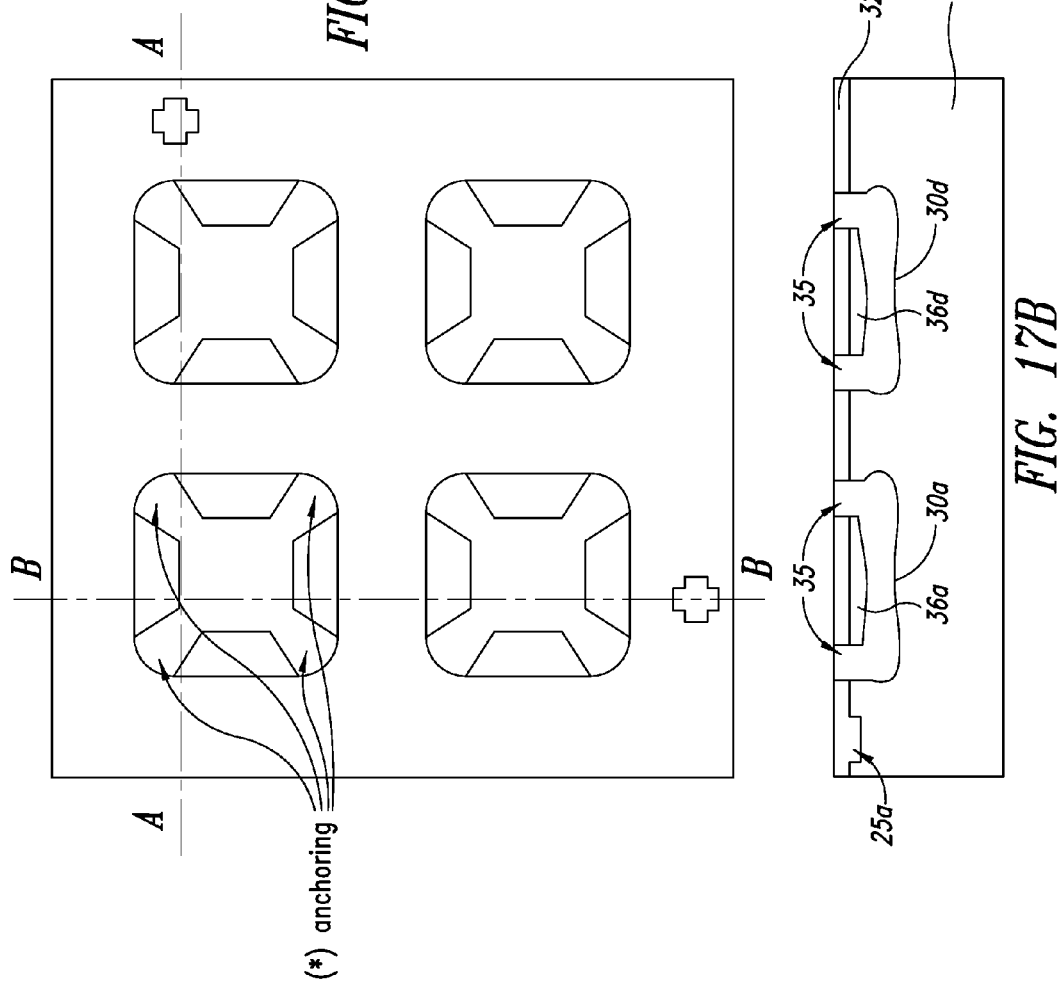
FIG. 17A
FIG. 17B
FIG. 17C

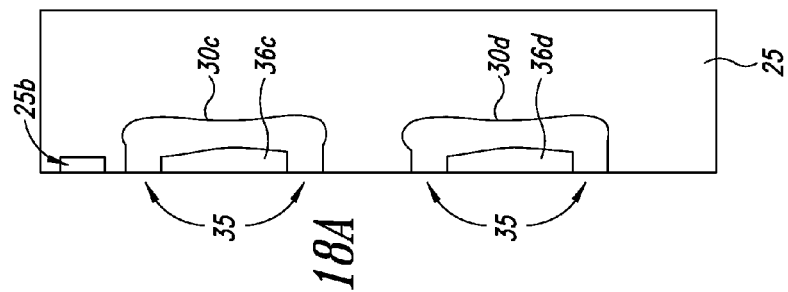
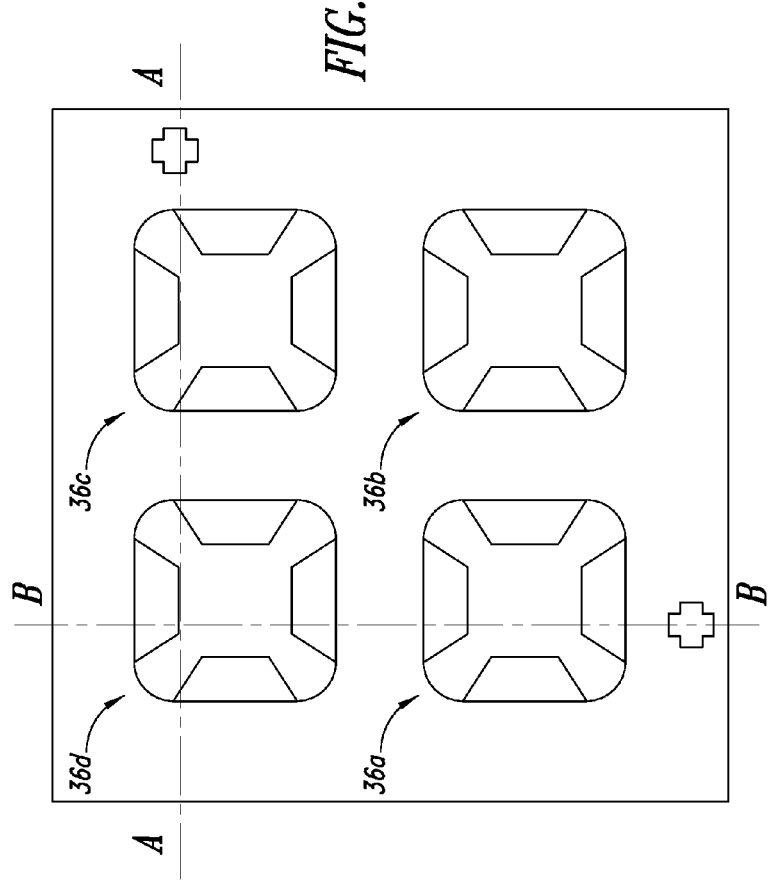

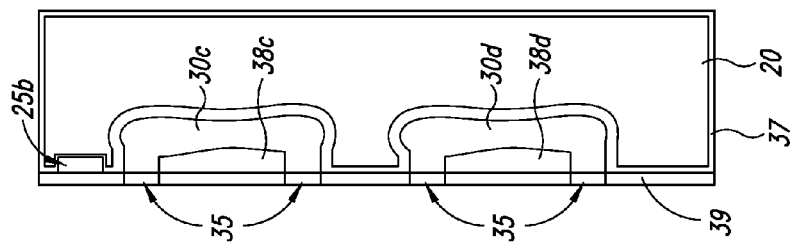
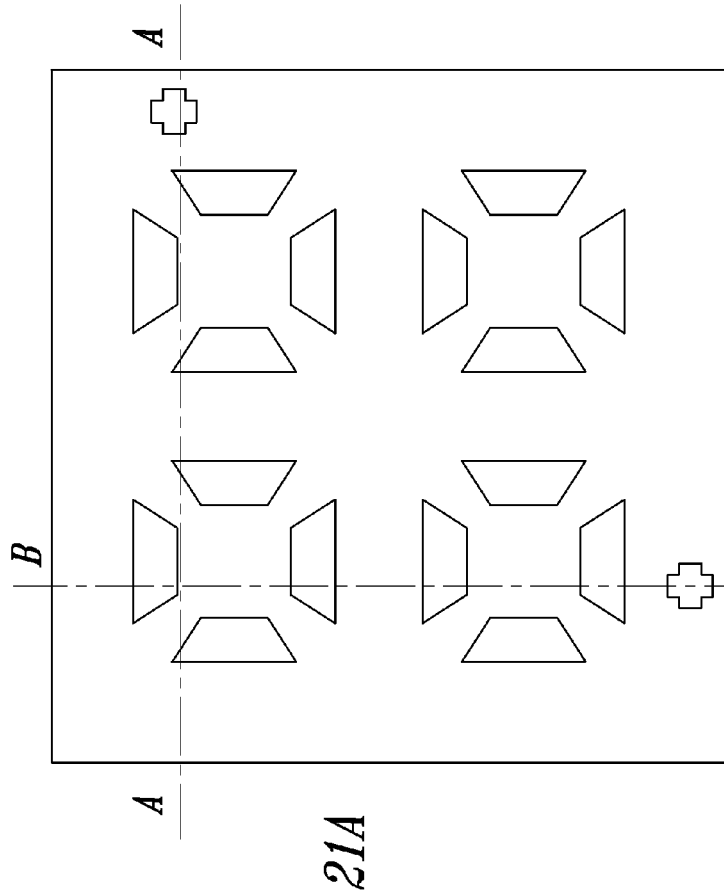
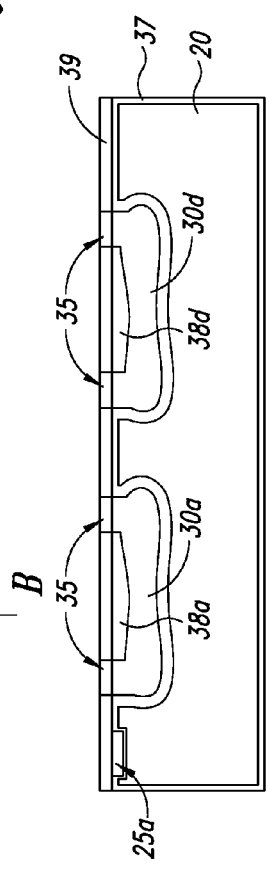
FIG. 21A
FIG. 21B
FIG. 21C

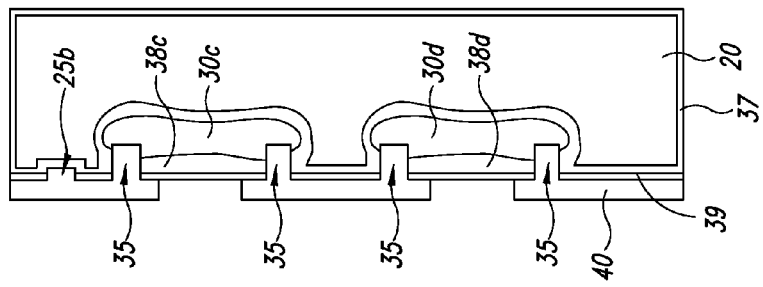
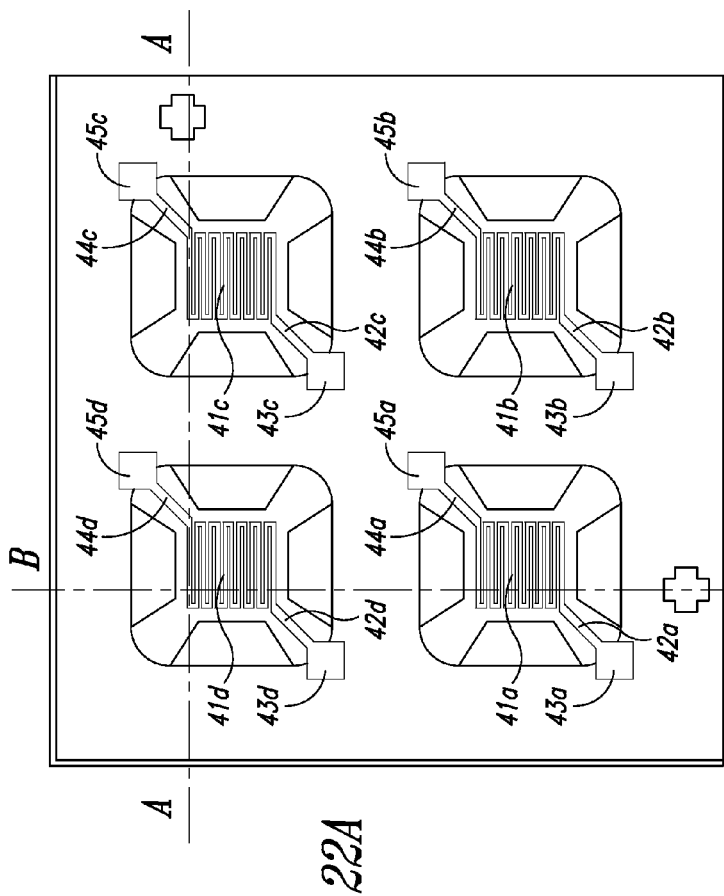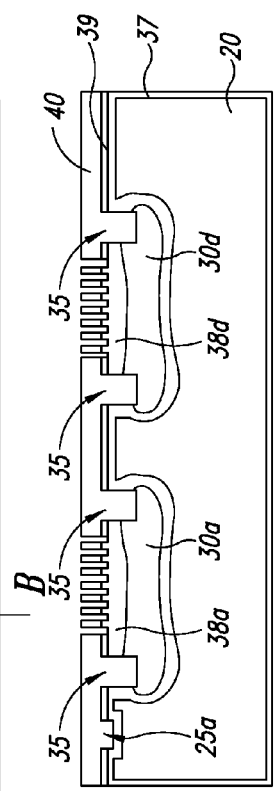
FIG. 22A
FIG. 22B
FIG. 22C

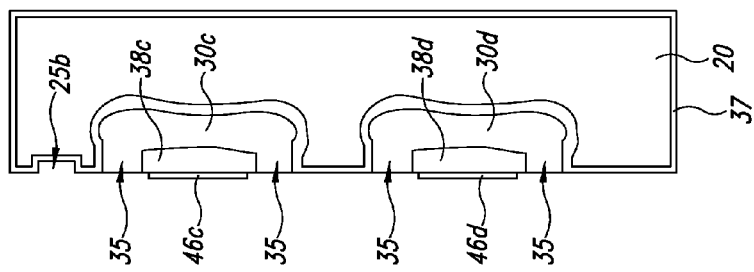
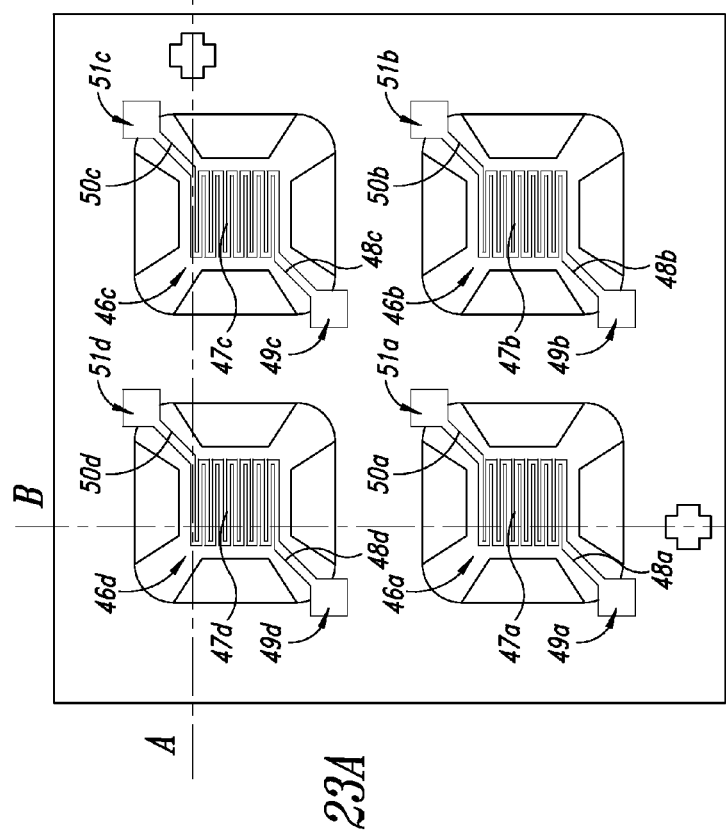
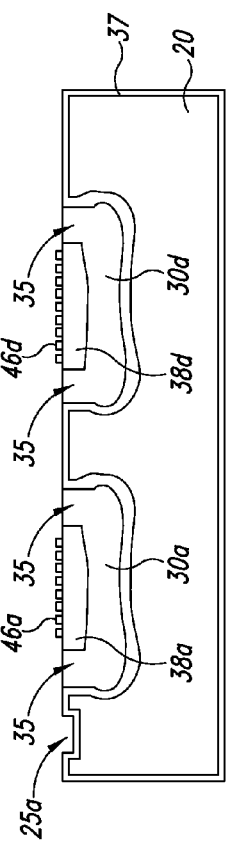

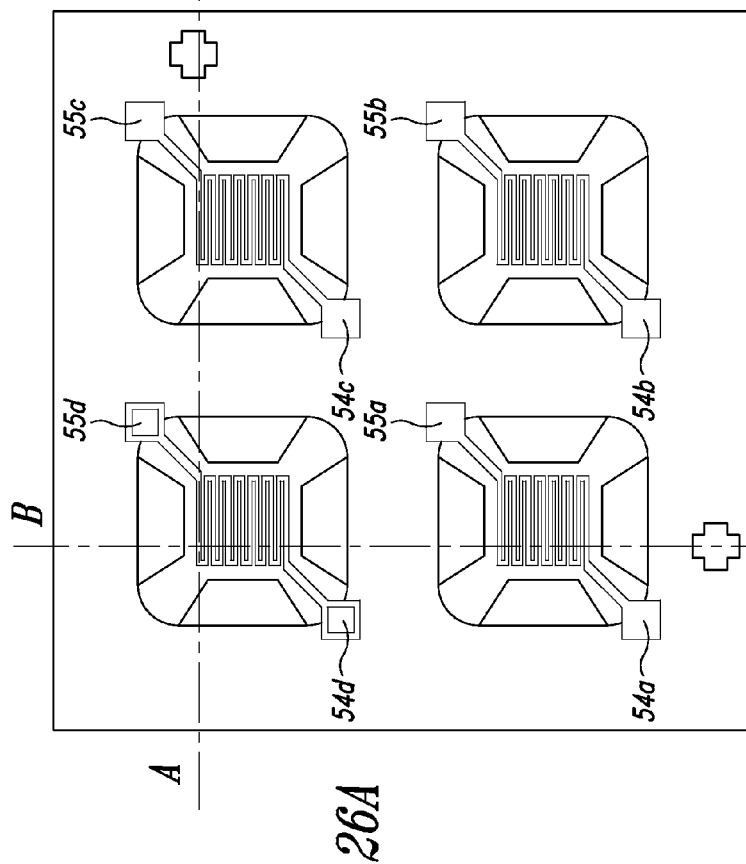
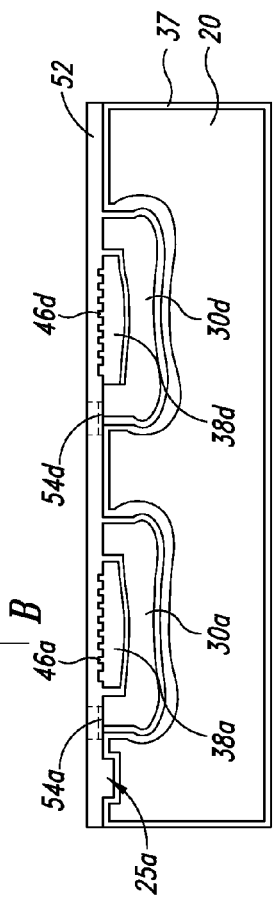
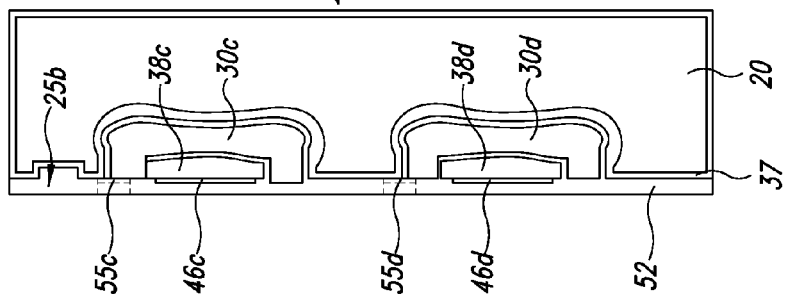
FIG. 26A
FIG. 26B
FIG. 26C

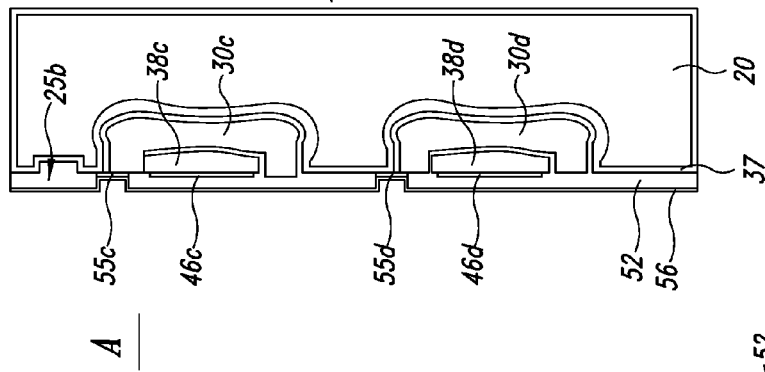
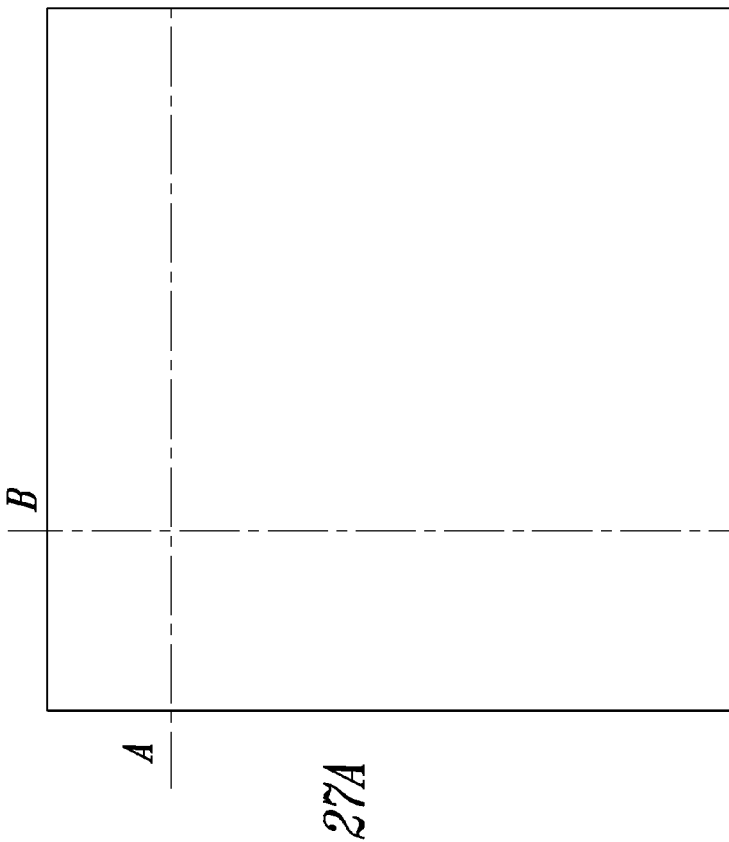
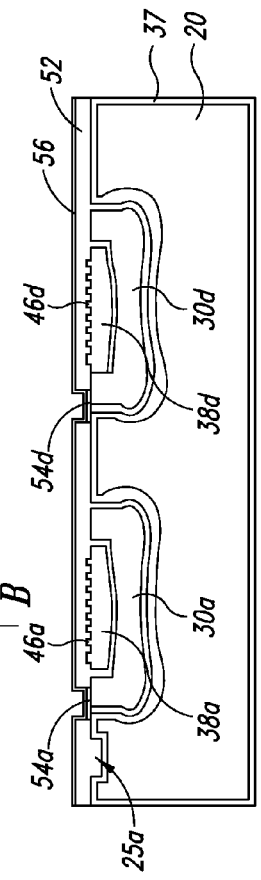

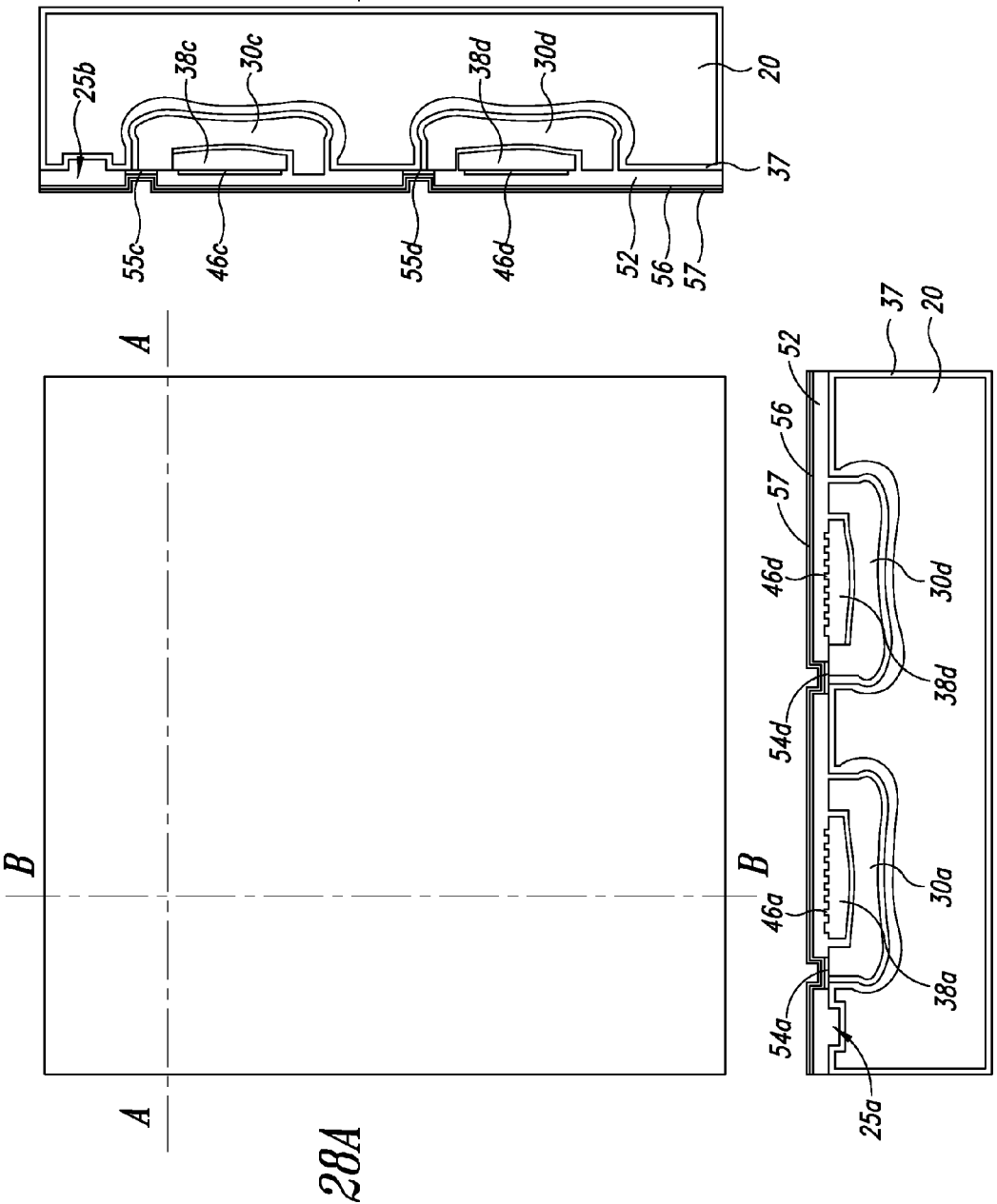

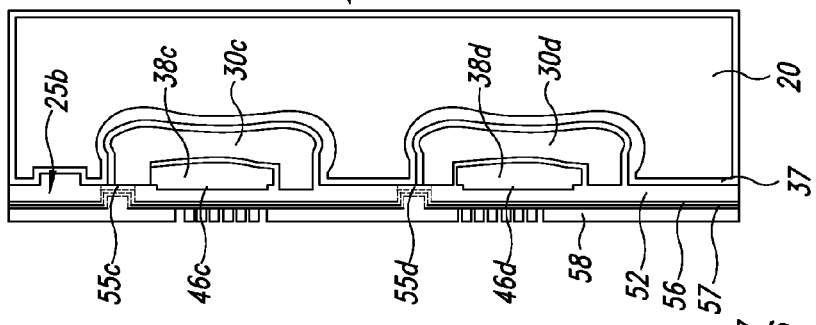
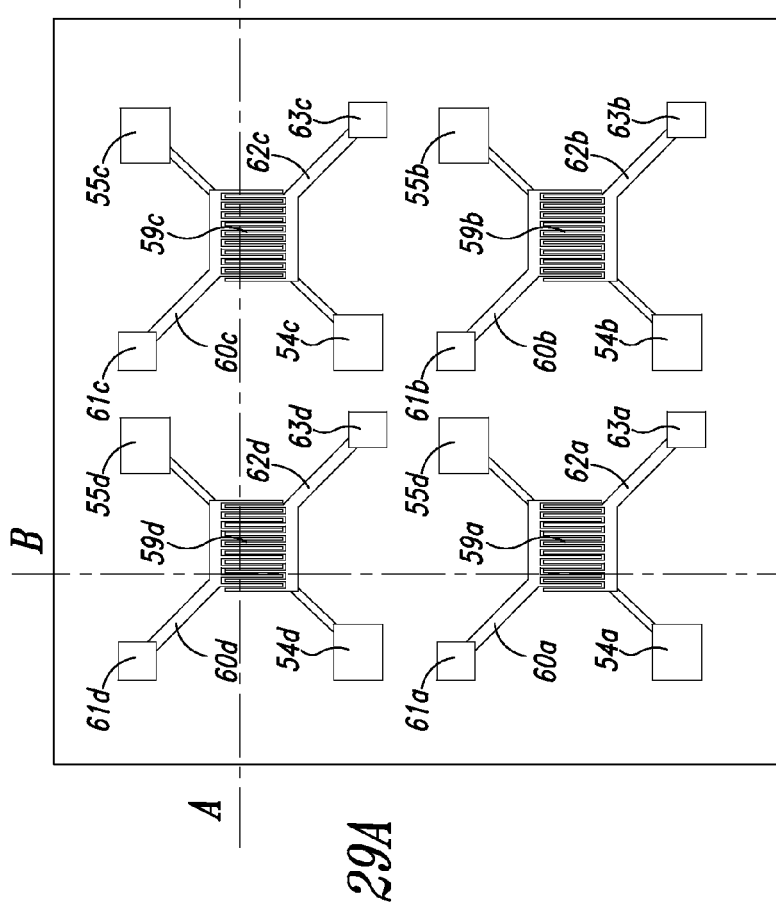
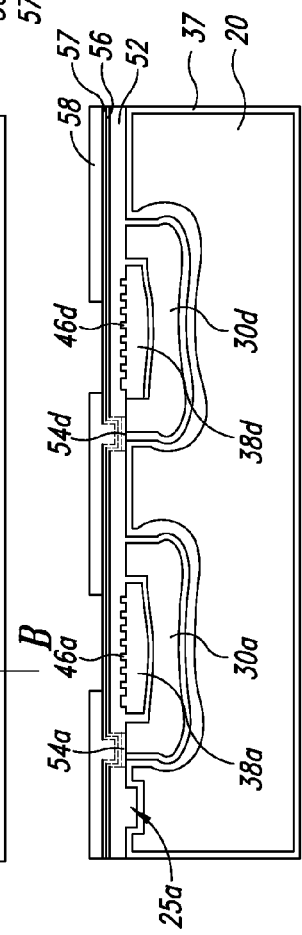
FIG. 29A
FIG. 29B
FIG. 29C

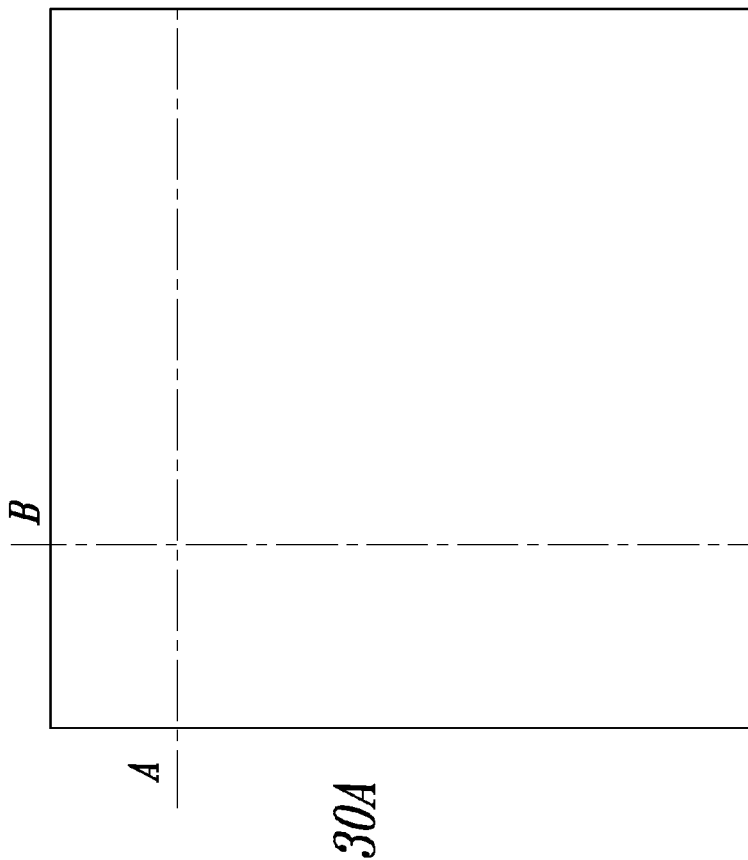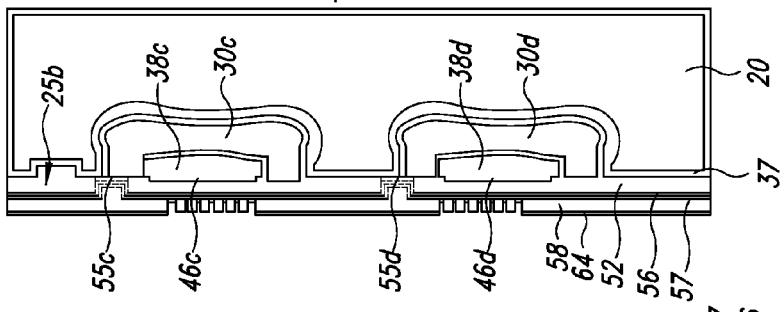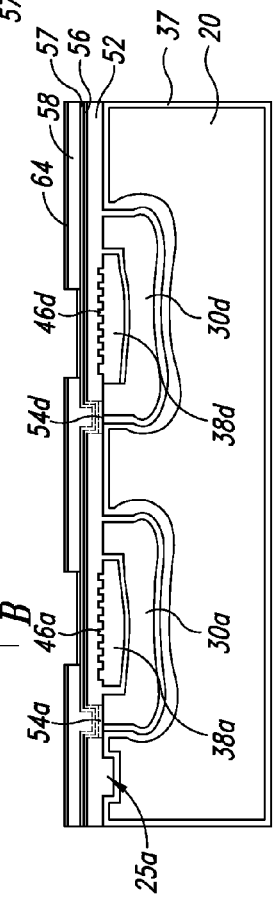

MANUFACTURING METHOD OF A GAS SENSOR INTEGRATED ON A SEMICONDUCTOR SUBSTRATE

BACKGROUND

1. Technical Field

The present disclosure relates to a method for manufacturing a gas sensor integrated on a semiconductor substrate.

The disclosure also relates to a dielectric membrane totally suspended on the semiconductor substrate whereon the gas sensor is integrated.

The disclosure particularly, but not exclusively, relates to a method for manufacturing a gas sensor integrated on a semiconductor substrate, of the type comprising a dielectric membrane suspended on the semiconductor substrate, a heating element and an element sensitive in metallic oxide (also nanostructured), and to the relative suspended dielectric membrane and the following description is made with reference to this field of application for convenience of illustration only.

2. Description of the Related Art

As it is well known, gas sensors comprise an element sensitive to volatile substances present in the environment, a heating element and some metallic electrodes. In particular, the fact that some materials change some of their chemical/physical/electric characteristics when they are in contact with other substances present in the environment surrounding them is exploited. This is the case of the resistivity variation of the material constituting the sensitive element which varies further according to the absorption of these volatile substances. The resistivity variations are measured by means of resistance measurements (voltage/current characteristics) between the electrodes in contact with the sensitive layer. In particular the variations are greater, and thus more easily detectable, when the sensitive element is brought, by the heating element, to a temperature comprised between 200° C. and 500° C. Higher temperatures are however exploited for the desorption of the substances for re-establishing on the sensor the initial conditions after the measurement.

Among the gas sensors, those whose sensitive element is formed by a nanostructured metallic oxide layer are well known, which are particularly suitable for detecting the presence of organic substances present in the surrounding environment. For example, it is known that the resistivity of a metallic oxide, such as the tin oxide ($SnO2$), varies up to three orders of magnitude if there are hydrocarbons, i.e., organic compounds containing only carbon and hydrogen.

At present, a gas sensor is integrated on a semiconductor substrate, together with the electrodes and the heating element, by means of the known semiconductor technologies. However, the integration on a single "chip" shows some problems, linked to the fact that, for detecting the variations of the electric characteristics of the sensitive element, this latter is at higher temperatures than the environment temperature, typically comprised between 200° C. and 500° C. However, the semiconductor substrate being a good heat conductor, the whole "chip" is subsequently brought to a high operation temperature, which, at the steady state, are practically identical to that of the sensitive element, which determines a considerable energy consumption by the heating element, as well as the malfunction and in some cases the irreversible damage of some of the components of the sensor itself or of other devices if the sensor is integrated with the control electronics or other circuitry.

To overcome this problem, a dielectric membrane is usually realized, serving as thermal insulator of the semiconductor substrate. A first known technical solution consists in realizing a gas sensor integrated on a semiconductor substrate, comprising a dielectric membrane suspended in the air, serving as thermal insulator and realized through the known "bulk micromachining" technique, which consists in the etching of the silicon in alkaline aqueous solutions, for example KOH (potassium hydroxide), NaOH (sodium hydroxide), TMAH (tetramethylammonium hydroxide). The dielectric membrane is then overhung by a heating element, above which the sensitive element is positioned, spaced from the heating element through a protective and insulating layer.

Although advantageous under several aspects, this first solution shows several drawbacks. In fact, the dielectric membrane is very fragile since it is realized through CVD deposition (Chemical Vapor Deposition) of a layer, generally of oxide or nitride or alternated silicon layers of these ones, which shows a high value of mechanical stress.

The fragility of the membrane also prevents from depositing the layer constituting the sensitive element by means of the known "screen printing" or "doctor blade" techniques.

Another drawback is due to the fact that this type of structure is realized through an anisotropic etching carried out from the back of the silicon wafer wherein the sensor is integrated, needing the use of a "double side" lithographic technique and generating, in the silicon itself, a section profile at 54.7°. Consequently, the space of the single device increases a lot. In fact, for realizing, for example, a squared suspended membrane of 100 μm of side on a substrate being 500 μm thick, it would be necessary to open from the back an etching window having a squared surface of more than 800×800 μm². Then, the space area of the device on the substrate would result much bigger than the one actually useful.

A second known solution consists of a gas sensor realized, instead, by means of the "surface micromachining" technique, which exploits an anisotropic etching of the basic type on the silicon substrate carried out from the front of the silicon wafer. In practice, a selective masking is carried out useful to leave, only in certain desired areas, a dielectric layer previously deposited on the whole silicon wafer. Alternatively, some sacrificial layers are used and some selective chemical etchings are carried out for the release of the membrane.

Although the described solution solves the problem of the increase of the space area, it does not eliminate, however, the problem linked to the stress and to the fragility of the suspended membranes realized by means of the CVD technique.

It is also known that, in the microelectronic industry, to favor the production and commercialization of systems, such as the gas sensors indeed, for the detection and the monitoring of gaseous agents it is important to considerably reduce the costs of the single items constituting them and to increase their reliability, sensitivity, specificity, stability and mechanical strength.

The self-organizing superficial atomic migration technique of the silicon allows to obtain mechanically strong suspended structures and to minimize the space of the devices.

An example of application of this technique is described in U.S. Pat. No. 7,193,256 of STMicroelectronics Srl, the assignee of the present application. In this application a method is described for manufacturing a semiconductor substrate comprising a buried insulating cavity, with the aim of realizing low cost SOI (Silicon On Insulator) structures. This method comprises the steps of: forming a plurality of openings in the semiconductor substrate; forming a superficial layer on the semiconductor substrate so as to superficially close the plurality of openings forming at the same time at least one buried cavity, in correspondence with the openings end distal from the surface. In particular, this cavity is realized starting from opening structures with cylindrical development realized, in the semiconductor substrate, by exploiting the properties of the self-organizing superficial migration process of the silicon.

In practice, after having realized openings with cylindrical development in the substrate, a thermal process is used ("annealing") at high temperature, for example between 1000° C.-1300° C., in non-oxidizing environment, for example $H_2$, for some tens of minutes.

FIGS. 1A to 1F show the modification steps, further to the thermal process, of the morphology of a opening 11 with cylindrical development realized in a substrate 10, which, as effect of the structural re-organization of the atoms towards minimum energy states, is transformed into a buried spherical cavity 11a, shown in FIG. 1F. FIGS. 2A to 2D show how very close openings 11 are first transformed into cavities of substantially "ninepin-like" shape to become, after, spherical cavities 11a which join the adjacent cavities thus forming a single space or microchannel 11b. In this way, an unlimited number of empty spheres 11a can be connected obtaining multiple geometries, as shown in FIGS. 3 and 4.

BRIEF SUMMARY

One embodiment is a method for manufacturing gas sensors integrated on a semiconductor substrate and the corresponding gas sensor, having such structural and functional characteristics as to obtain a high sensitiveness of the gas sensor with low cost manufacturing processes overcoming the limits and/or the drawbacks still affecting the gas sensors realized according to the prior art.

One embodiment is a method for manufacturing a gas sensor integrated on a semiconductor substrate, comprising a dielectric membrane totally suspended on the semiconductor substrate, a heating element, electrodes and a sensitive element comprising metallic oxides. The suspended dielectric membrane is realized through thermal oxidation of a totally suspended thin crystalline silicon layer covering a buried cavity formed, in a semiconductor substrate, starting from opening structures, as effect of the known self-organizing superficial migration process of the silicon. Moreover, the sensitive element is formed by a layer of metallic oxides which can be subjected to a sintering process, which occurs inside the silicon wafer wherein the sensor is integrated, thanks to the interconnection of the heating elements.

One embodiment is a method that comprises the steps of:
realizing a first plurality of openings in said semiconductor substrate;
realizing a crystalline silicon membrane suspended on said semiconductor substrate, forming at the same time at least one insulating cavity buried in said substrate;
realizing a second plurality of openings in said semiconductor substrate, so as to totally suspend on said semiconductor substrate said at least one crystalline silicon membrane;
realizing, through a thermal oxidation process of said at least one totally suspended crystalline silicon membrane, said at least one suspended dielectric membrane;
realizing, through selective photolithography, said at least one heating element;
realizing, through selective photolithography, said at least one electrode and said at least one pair of electric contacts;
selectively realizing, above said at least one electrode, said at least one sensitive element, comprising the step of compacting said metallic oxide layers through a sintering process generated in said at least one gas sensor by connecting said at least one electrode with a voltage generator.

One embodiment includes a dielectric membrane suspended on said substrate and is realized through a thermal oxidation process of at least one crystalline silicon membrane totally suspended on said substrate.

The characteristics and the advantages of the method and of the membrane device will be apparent from the following description of an embodiment given by way of indicative and non-limiting example with reference to the annexed drawings.

BRIEF DESCRIPTION OF THE SEVERAL VIEWS OF THE DRAWINGS

In these drawings:

FIGS. 1A to 1F are respective schematic views of a opening realized in a semiconductor substrate during the successive steps of a manufacturing method, according to the prior art;

FIGS. 2A to 2D are respective schematic views of a plurality of openings realized in a semiconductor substrate during the successive steps of a manufacturing method, according to the prior art;

FIGS. 3 and 4 show possible geometries of cavities that can be obtained starting from openings differently arranged, according to the prior art;

FIGS. 5(A-C) to 18(A-C) and 20(A-C) to 33(A-C) show the schematic plan views and the two section views, longitudinal in the plane AA' and transversal in the plane BB', of a portion of semiconductor substrate during the successive steps of a manufacturing method of a gas sensor, according to one embodiment;

DETAILED DESCRIPTION

With reference to these figures, the method is described for manufacturing a gas sensor integrated on a semiconductor substrate, according to one embodiment.

In particular, FIGS. 5A-5C shows a semiconductor substrate 20, realized by a crystalline silicon wafer with any crystallographic orientation of the P type, for example doped with acceptor ions having concentration comprised between 1E13 and 5E20 [$cm^{-3}$] (type $P^-$, P, $P^+$, $P^{++}$, etc.). Alternatively, the semiconductor substrate 50 is doped with donor ions (N type) having concentration, for example, comprised between 1E13 and 5E20.

Figure 6C:
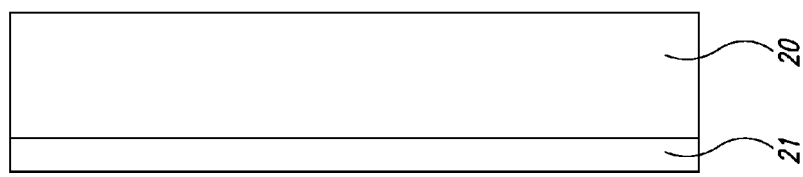
Figure 6A:
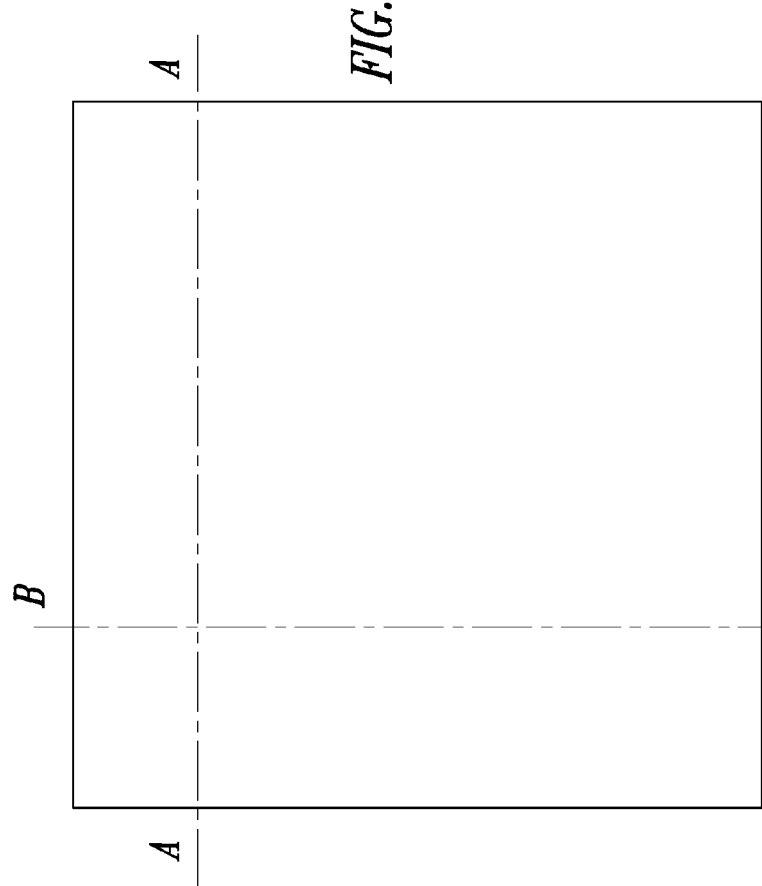
Figure 6B:
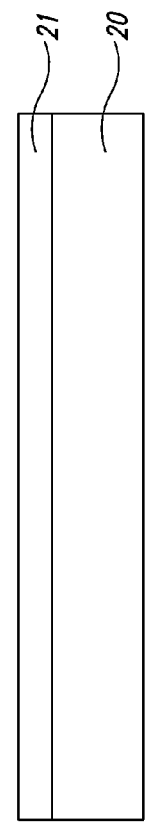

In an initial step, the silicon wafer is subjected to chemical washing, with the aim of removing organic materials and possible residues of powders present on the surface, and, subsequently, to a first conventional photo-lithography step, which occurs, as shown in FIGS. 6A-6C, with the use of a first masking dielectric layer 21 deposited on the whole surface of the substrate 20. The dielectric layer 21 is formed by a silicon oxide or, alternatively, nitride or, alternatively, photoresist or, alternatively by a combination of these materials, which are deposited, alternatively, grown according to known processes of the microelectronic technology. Further, as shown in FIGS. 7A-7C, a photomasking is carried out by depositing on the dielectric layer 21a first photoresist layer 22, so as to leave exposed a first portion 23a of the layer 21 overhanging a first portion 24a of the substrate 20, shown in the longitudinal section of FIG. 7B, and a second portion 23b of the layer 21 overhanging a second portion 24b of the substrate 20, shown in the cross section of FIG. 9C.

Figures 8A, 8B, 8C:
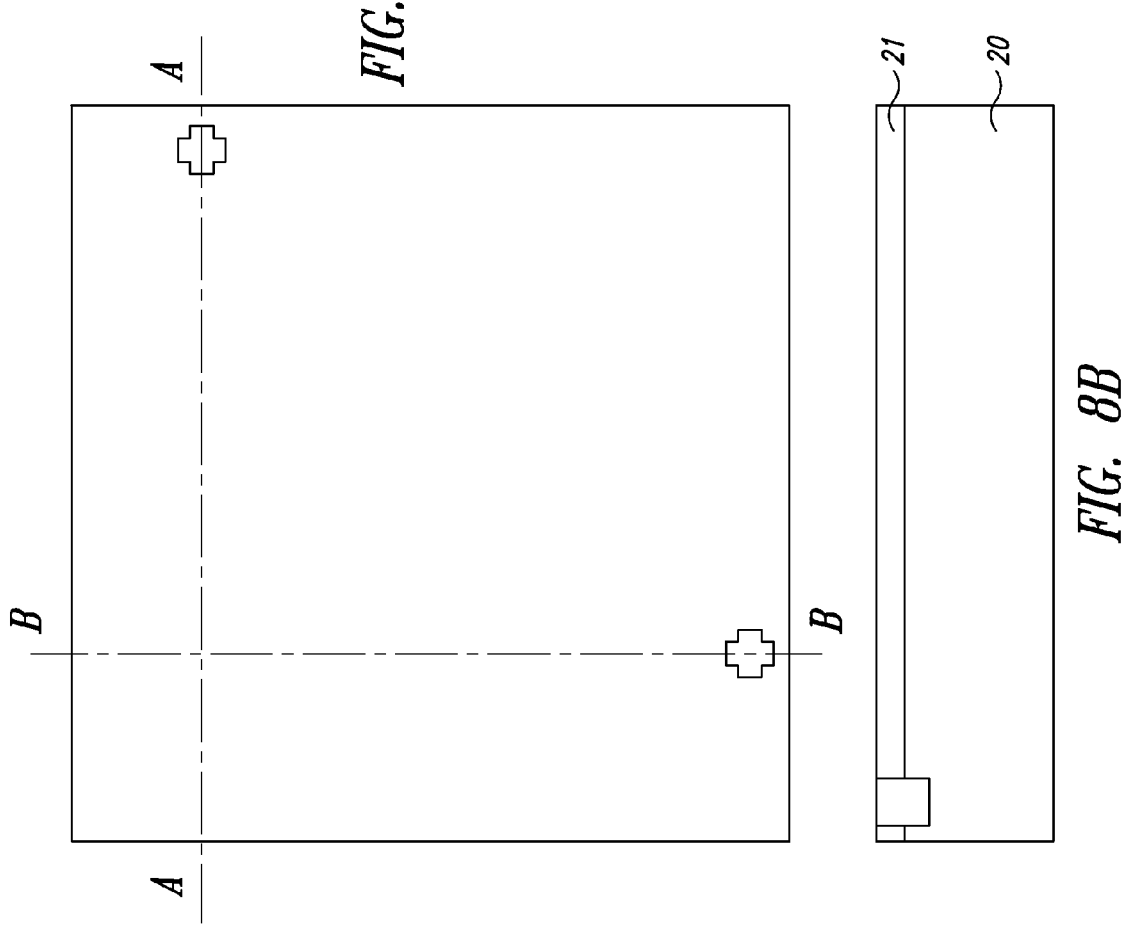

FIGS. 8A-C show the structure resulting from the successive carrying out of: a chemical etching step, wet or dry, of the dielectric layer 21, which eliminates the portions 23a and 23b; a removal step of the photoresist layer 22; and an etching step of the first portion 24a and of the second portion 24b of the silicon substrate 20. Finally, the dielectric layer 21 is totally removed from the whole surface of the substrate 20, wherein a first opening 25a, shown in FIG. 9B, and a second opening 25b, shown in FIG. 9C, remain. These openings constitute reference signs in the substrate, useful for the alignment of all the lithographic levels used during the successive manufacturing steps of the gas sensor.

According to another embodiment, instead, the first photolithography step occurs by directly using the photoresist layer 22 as masking material and by etching the substrate 20 with a chemical etching, wet or dry.

Figure 10C:
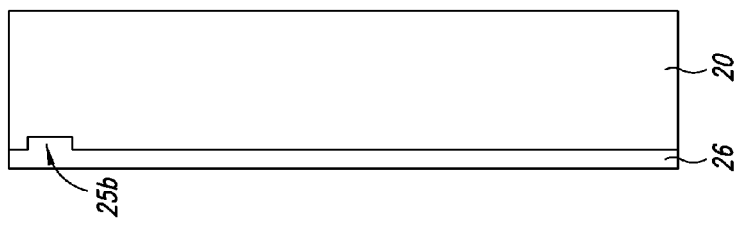
Figure 10A:
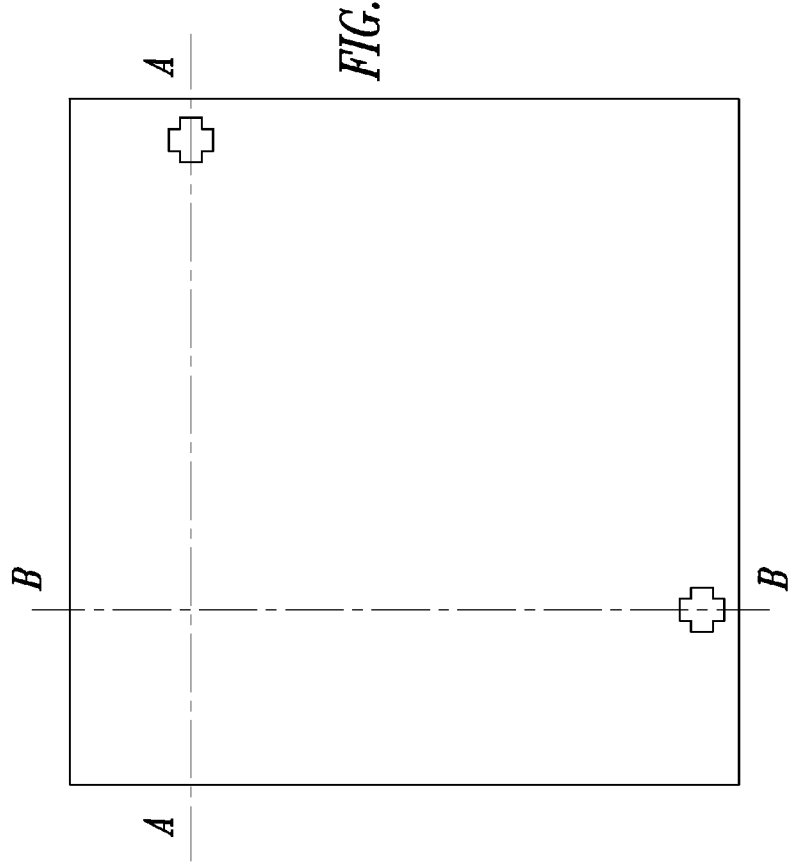
Figure 10B:
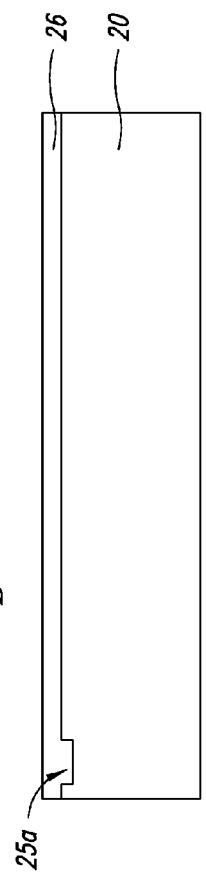
Figure 12C:
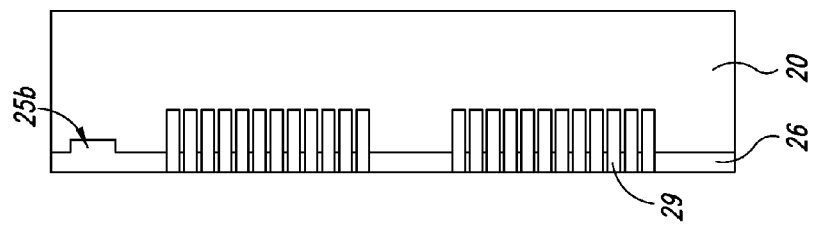
Figure 12A:
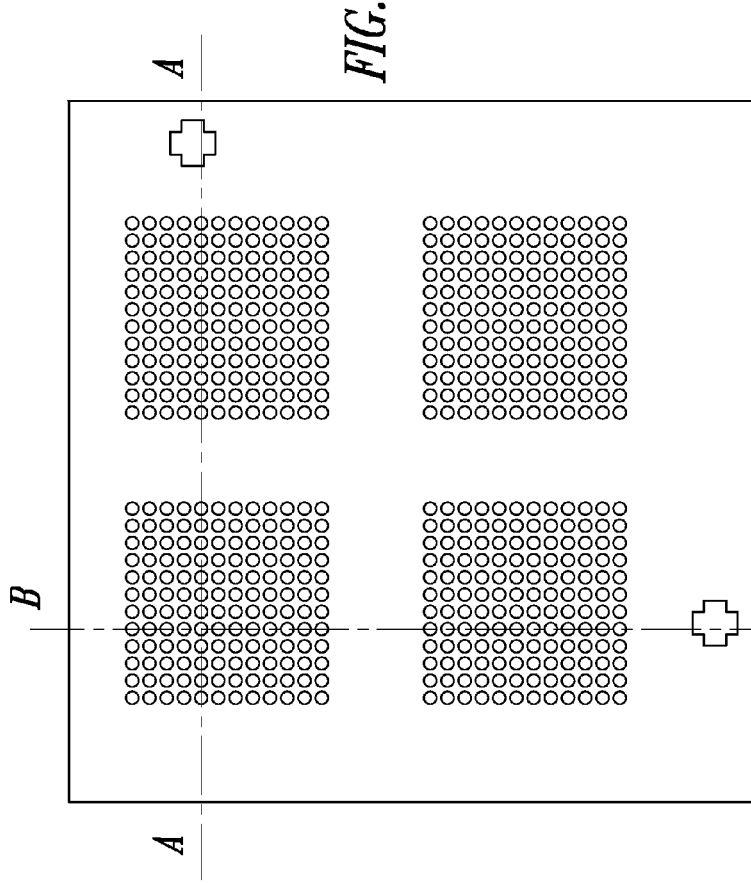
Figure 12B:
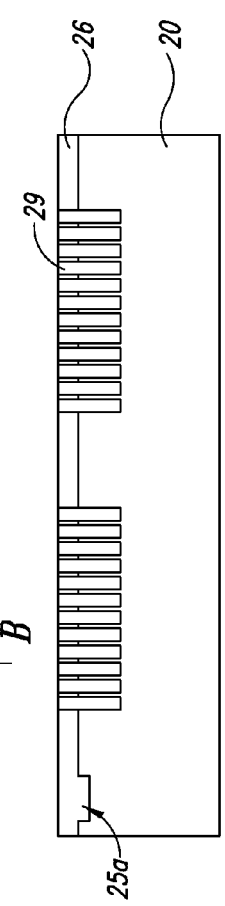

The method goes on with the realization, in the substrate 20, of a first plurality of openings. In particular, on the surface of the substrate 20 and even inside the openings 25a and 25b, a second dielectric layer 26 is deposited, as shown in FIGS. 10A-C. Subsequently, a second photolithographic step is carried out, by depositing, as shown in FIGS. 11A-C, a second photoresist layer 27 in a selective way on the dielectric layer 26, leaving exposed four pluralities 28a-28d of suitably spaced cylindrical holes, forming squared regions (obviously, the geometries manufactured with this method can be of any shape), as it is particularly clear from FIG. 11A. As shown in FIGS. 12A-C, an etching step of the dielectric layer 26, a removal step of the photoresist layer 27 and an etching step of the substrate 20 follow. In this way, a first plurality of equidistant openings 29 having cylindrical development is realized, the openings having a width comprised between 0.3 µm and 2 µm and a depth comprised between 2 µm and 100 µm. The openings 29 can, alternatively, be realized in the shape of a parallelepiped or of any other polygonal solid, by modifying the geometry of the areas exposed from the photoresist layer 27. The distance between the centers of two consecutive openings 29 is proportional to the width of the openings themselves with a proportionality factor comprised between 1.1 and 3. The geometric arrangement of the openings 29 in the substrate 20 directly depends on the geometry with which the photoresist layer 27 has been deposited and influences the geometry of the membrane of the gas sensor, realized in successive steps.

Figures 13A, 13B, 13C:
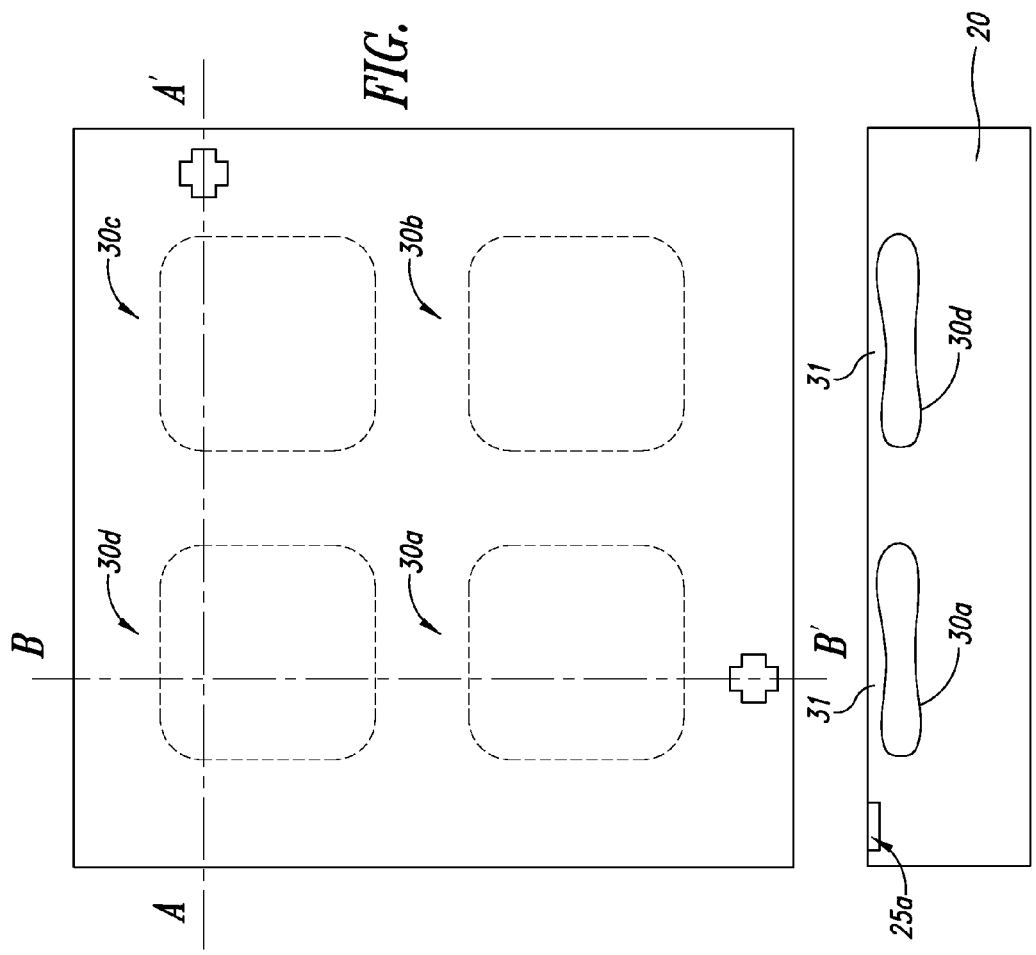

Once the first plurality of openings 29 has been defined, the substrate 20 is subjected, first, to a removal step of the dielectric layer 26 and, further, to a thermal process with hydrogen at high temperature, comprised between 1000° C. and 1300° C. The resulting structure is shown in FIGS. 13A-C. This thermal process, as it is known, determines the structural re-organization of the silicon atoms towards minimum energy states, thanks to the known phenomenon of the self-organizing superficial atomic migration of the silicon, which modifies the shape of the openings 29 from cylindrical to spherical. Moreover, the openings 29 are realized so that the distance between their centers is lower or at the most equal to the diameter of the sphere formed by each opening 29, thereby all the spheres merge, forming a cavity buried in the substrate without causing reticular defects and mechanical stress in the crystalline silicon overhanging the cavity which is rearranged naturally towards a minimum energy state. Moreover, if the openings 29 are very deep with respect to their width, the thermal process determines the formation of different cavities vertically aligned and separated by foils of crystalline silicon. In particular, as shown in FIG. 13A four cavities 30a-30d are formed, buried into the substrate 20 and separated by foils of crystalline silicon. FIG. 13B shows the longitudinal sections of a first and a fourth cavity 30a and 30d and FIG. 13C shows the cross sections of a third cavity 30c and the fourth cavity 30d. Also the shape of the cavities depend on the geometry of the openings 29. The buried cavity also has squared shape. The assembly of the foils of crystalline silicon covering the four cavities and anchored to the substrate 20 only peripherally and by thin crystalline silicon structures between the buried cavities 30a-30d, forms a crystalline silicon membrane 31 partially suspended on the substrate 20. In the case of big surface sizes, to avoid the collapse of the superficial layer on the underlying one, support points are provided being obtained by eliminating isolated points, segments, lines or small areas from the geometry of the openings, trying to maintain however connection points between the various cavities as formed, i.e., to avoid the collapse of the suspended structure overhanging the cavity, a single point or line or a small area can be eliminated from the array of openings, so that the lack of the openings in these points does not realize a spherical cavity, which will then leave a column of substrate which will serve as a pilaster for the overhanging membrane.

Figure 15C:
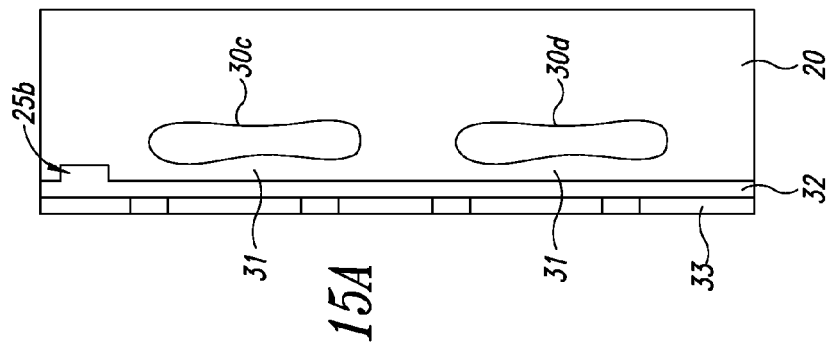
Figure 15A:
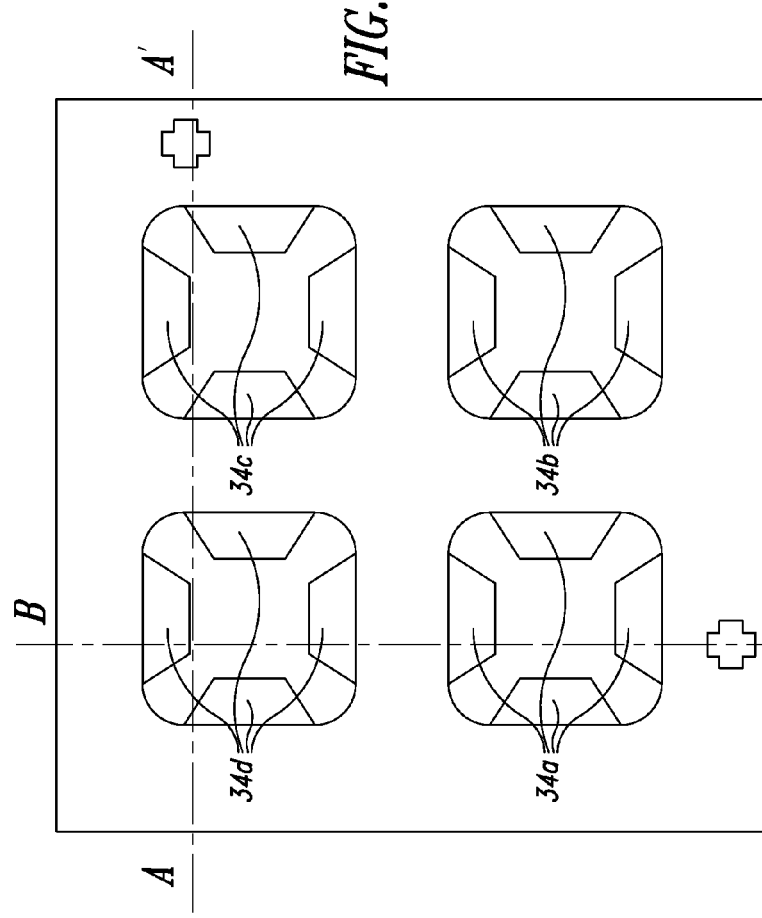
Figure 15B:
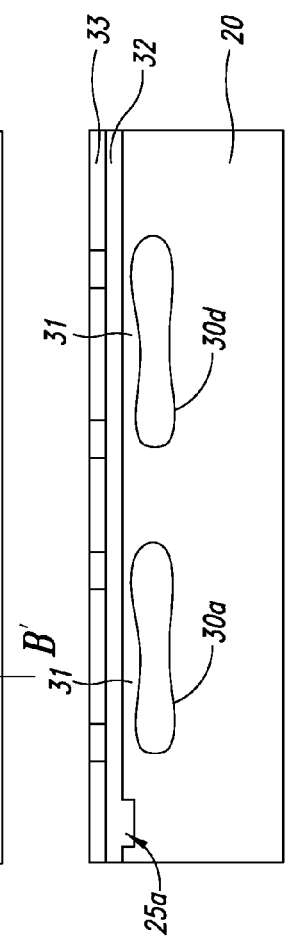

The method goes on with the realization of a second plurality of openings. Then a step is carried out, shown in FIGS. 14A-C, in which the substrate 20 is covered with a third masking dielectric layer 32. Further, as it is particularly clear from FIGS. 15A and 15B, a third photoresist layer 33 is deposited on the dielectric layer 32, leaving exposed four trapezoidal regions thereof (of any shape) 34a-34d in correspondence, respectively, with each one of the buried cavities 30a-30d. According to another embodiment, instead, the photolithography step suitable for realizing the second plurality of openings occurs by using the photoresist layer 33 as a masking layer.

Figure 16C:
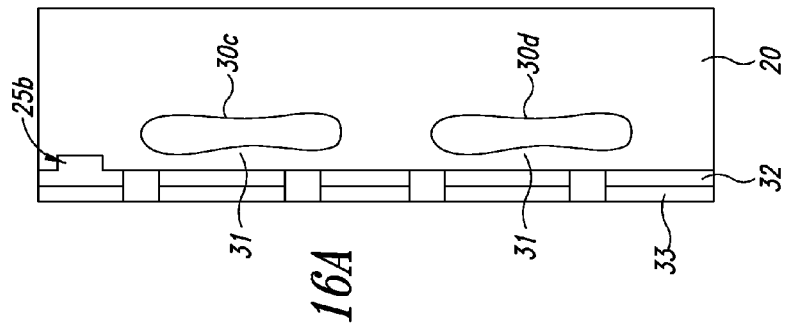
Figure 16A:
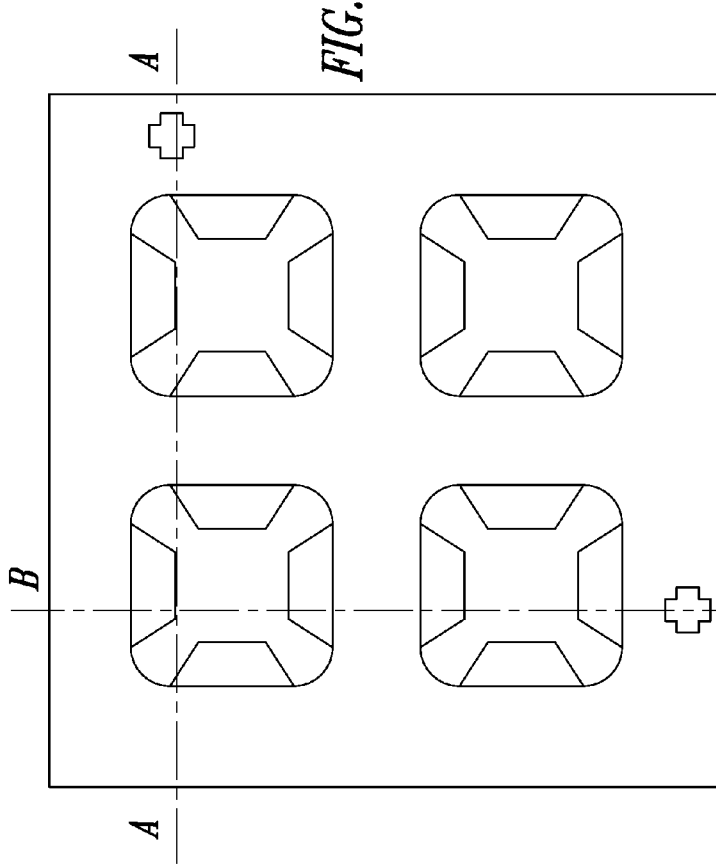
Figure 16B:
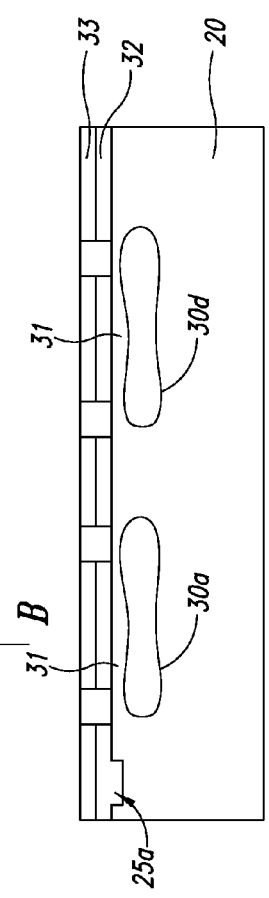

The method goes on with an etching step of the dielectric layer 32, as shown in FIGS. 16A-16C, and, with the steps of removal of the photoresist layer 33 and of chemical etching, wet or dry, of the silicon substrate 20, as shown in FIGS. 17A-C. In this way, a second plurality of openings 35 is formed, by transforming, at the same time, the crystalline silicon membrane 31 suspended and peripherally anchored to the substrate into a crystalline silicon membrane totally suspended on the substrate except for some anchoring points (see FIGS. 17A-C), and covered by the dielectric layer. In particular, FIG. 17B show the longitudinal sections of a first and of a second suspended membrane 36a and 36b and FIG. 17C the cross sections of a second and a third suspended membrane 36b and 36c. Finally, by removing the masking dielectric layer 32, four crystalline silicon membranes 36a-36d, totally suspended and anchored onto the substrate, are clear, as shown in FIG. 18A.

Figure 19:
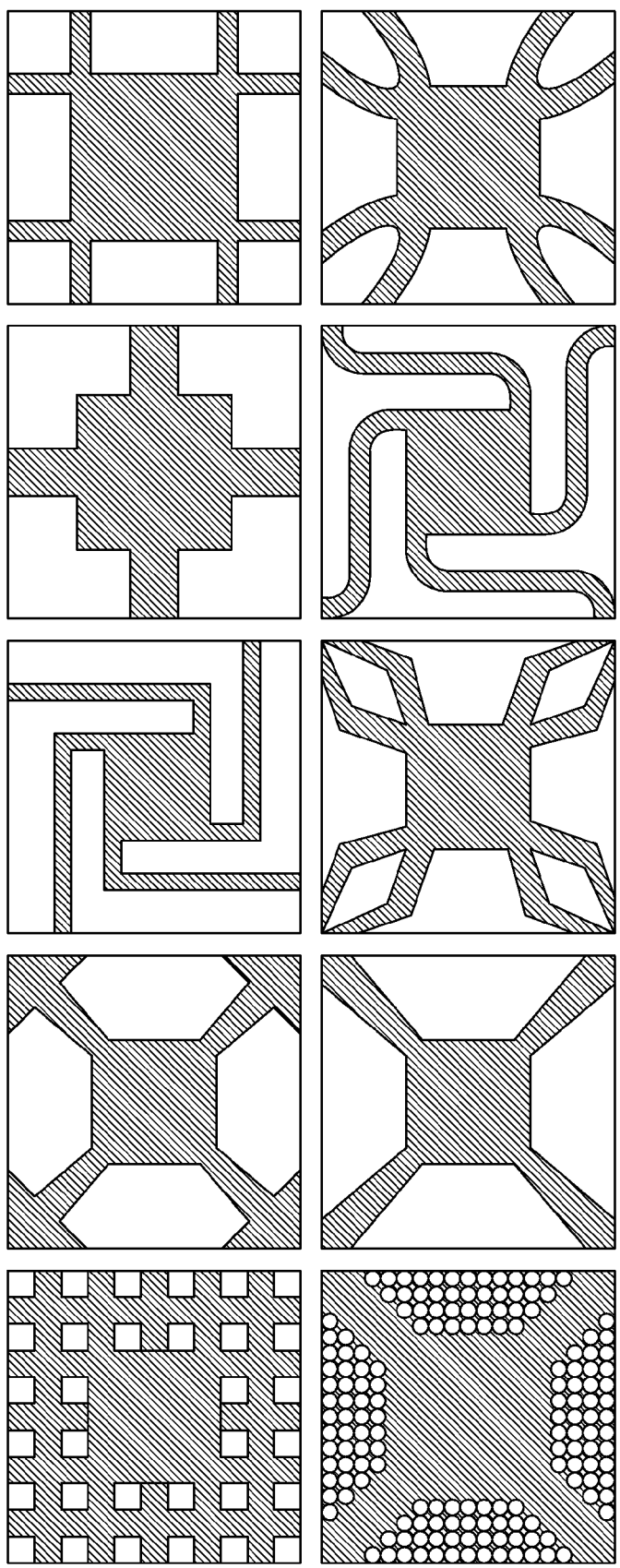
FIG. 19 shows possible geometries of a crystalline silicon membrane suspended on the semiconductor substrate, according to one embodiment.

FIG. 19 shows, only by way of example, some of the possible geometries of the suspended crystalline silicon membranes 36a-36d. In particular, the clear areas of the geometric shapes of FIG. 19 are defined by the first plurality of openings 29, while the shaded areas by the second plurality of openings 35. The final shape of the suspended membrane is the shaded part.

The clear areas of the geometric shapes of FIG. 19 are the openings 35 created in the membrane suspended over the buried cavity formed after the thermal process in hydrogen and structural re-organization, involving silicon and the plurality of openings 29. The final shape of the suspended membrane is the shaded part.

Figure 20C:
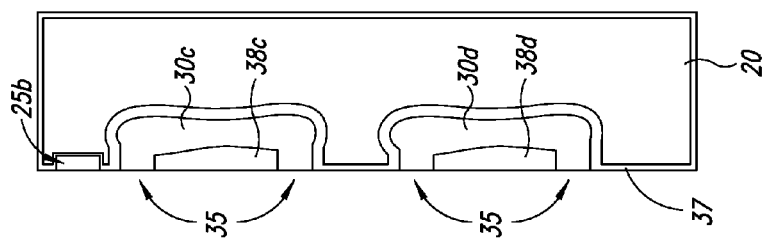
Figure 20A:
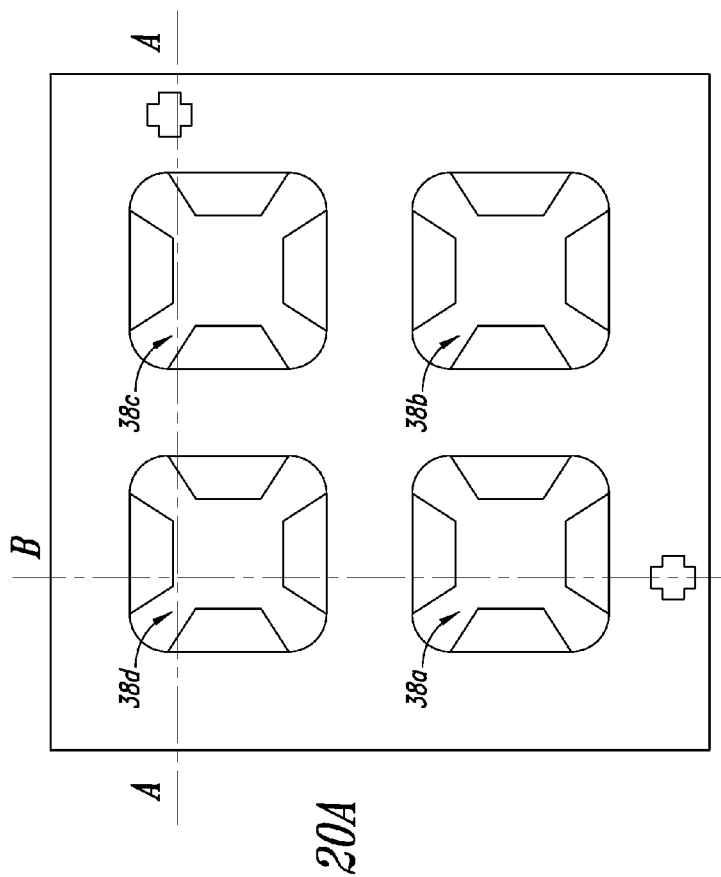
Figure 20B:
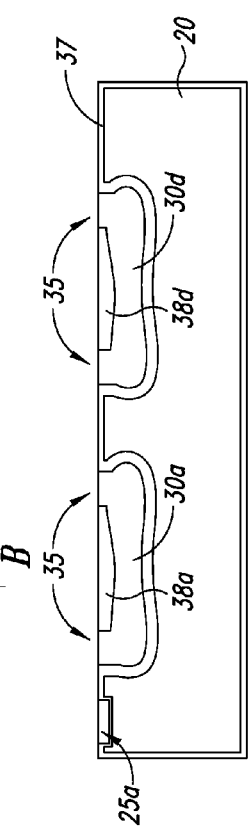

The method goes on with the total oxidation of the suspended membranes 36a-36d, with the aim of thermally insulating the substrate 20 of the gas sensor. To this aim, as shown in FIGS. 20A-C, a thermal process is carried out at high temperature (between 800 and 1300° C.) in atmosphere containing oxygen, forming a thermal oxide 37 on all the surfaces of the substrate 20, inside the openings 35, below the cavities 30a-30d and on the suspended crystalline silicon membranes 36a-36d. In this way, the total oxidation is realized of the suspended crystalline silicon membranes 36a-36d (from both the surfaces of the membrane, then the oxidation will go on both from the surface and from the cavity), obtaining suspended dielectric membranes 38a-38d, shown in FIG. 20A, completely constituted by thermal oxide and having thicknesses of several microns. For example, for a crystalline silicon membrane being 2 μm thick, the suspended dielectric membrane obtained has a thickness of about 4 μm. FIG. 20B shows the longitudinal sections of a first and of a second suspended dielectric membrane 38a and 38b and FIG. 20C shows the cross sections of a second and of a third suspended dielectric membrane 38b and 38c.

Advantageously, the suspended dielectric membranes can be realized both on the front and on the back of the silicon wafer thanks to the photolithographic technique known as "Double Side Mask aligner".

The method goes on, then, with the realization of one or more heating elements, completed with the connection branches and with the contact and interfacing areas. The heating elements are realized by a conductive material chosen between aluminum, gold, polysilicon or other metals, according to the application and to the maximum desired temperature, so that, if crossed by an electric current, an amount of heat is developed, through Joule effect, proportional to the temperature to be obtained on the sensitive element, the dielectric membranes serve as thermal insulator towards the substrate 36a-36d.

Moreover, the method also provides, in one aspect, the integration, in the gas sensor, of one element of the thermo-resistive type which continuously monitors the temperature attained by the suspended dielectric membranes 36a-36d.

Then, a layer 39 is deposited, of conductive material, for example polysilicon doped with LPCVD techniques in kiln or by means of epitaxial growth techniques (EPYPOLY), as shown in FIGS. 21A-C. Further, as shown in FIGS. 22A-C, a fourth photoresist layer 40 is deposited, in a selective way, on the polysilicon layer 39, leaving exposed, in correspondence with the suspended dielectric membranes 36a-36d, a region 41a-41d of coil-like shape or other shape to realize the heater on the membrane, in any case a conductive path will be realized which will exploit the Joule effect, taking care of bringing the extremes of said path out of the suspended area and thus on the substrate, where the electric contacts will be realized, making the heater path pass above the anchoring structures of the membrane, having a first end ending, through a first oblique arm 42a-42d, in a first squared region 43a-43d and a second end ending, through a second oblique arm 44a-44d, in a second squared region 45a-45d, as it is clear from FIG. 22A. Subsequently, as shown in FIGS. 23A-C, a chemical etching step, wet or dry, of the layer 39 and a removal step of the photoresist layer 40 are carried out. In this way, the heating elements 46a-46d are formed, shown in FIG. 23A, respectively placed above the suspended dielectric membranes 38a-38d and constituted by polysilicon nanostructures. The heating elements 46a-46d have a geometry determined by the photolithography and, in particular, comprise a region 47a-47d generally with a coil-like shape, or of any other shape, having a first end ending, through a first oblique arm 48a-48d, in a first squared region 49a-49d and a second end ending, through a second oblique arm 50a-50d, in a second squared region 51a-51d. FIG. 23B shows the longitudinal sections of a first and of a fourth heating element 46a and 46d. FIG. 23C shows the cross sections of a third heating element 46c and the fourth heating element.

Figure 24C:
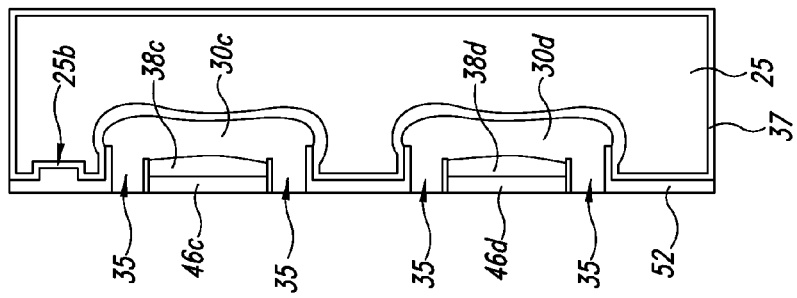
Figure 24A:
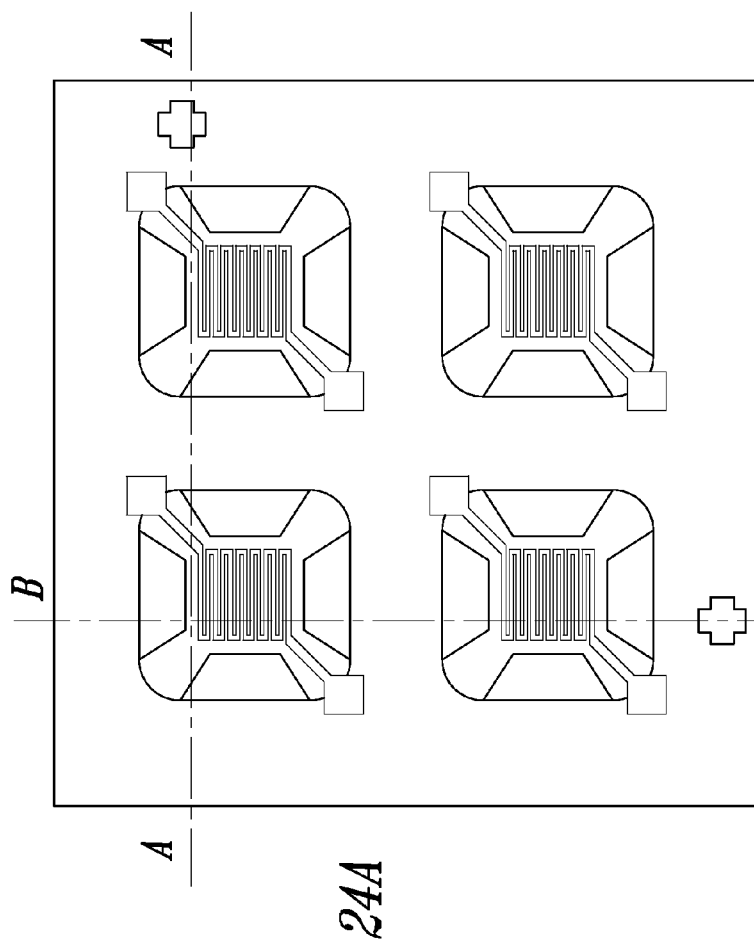
Figure 24B:
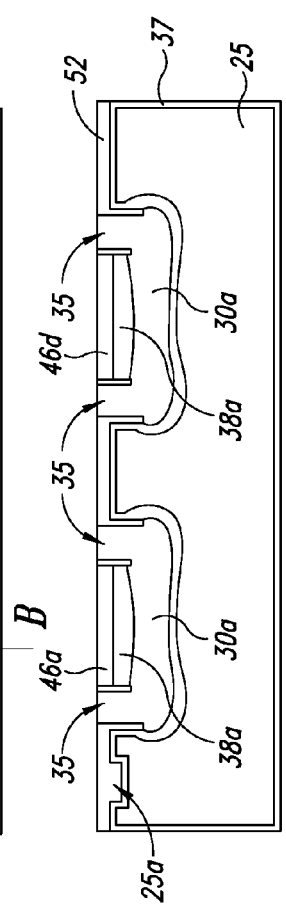

Subsequently, as it is clear from FIGS. 24A-C, a deposition is carried out, according to one of the known PECVD (Plasma Enhanced Chemical Vapor Deposition) or LPCVD (Low pressure Chemical Vapor Deposition) or PVD (Physical Vapor Deposition) techniques, of a fourth thin dielectric layer 52, for example $SiO_2$, TEOS, Vapox, nitride, etc. This layer having the function of an electric insulator of the heating element, in case this latter is realized with polysilicon and not through deposition of a metallic layer, it can also be obtained through partial oxidation of the polysilicon layer itself. The dielectric layer 52, which serves as passivator, uniformly covers all the heating elements 46a-46d, also entering into the openings 35, and has a thickness comprised between some thousands of Angstroms and several microns, according to the material it is made of, to the deposition technique and to the application.

Figure 25C:
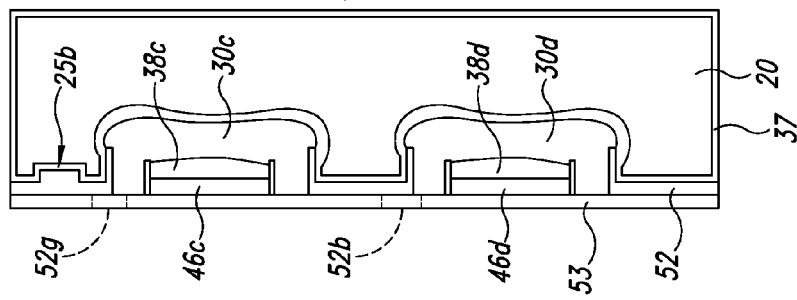
Figure 25A:
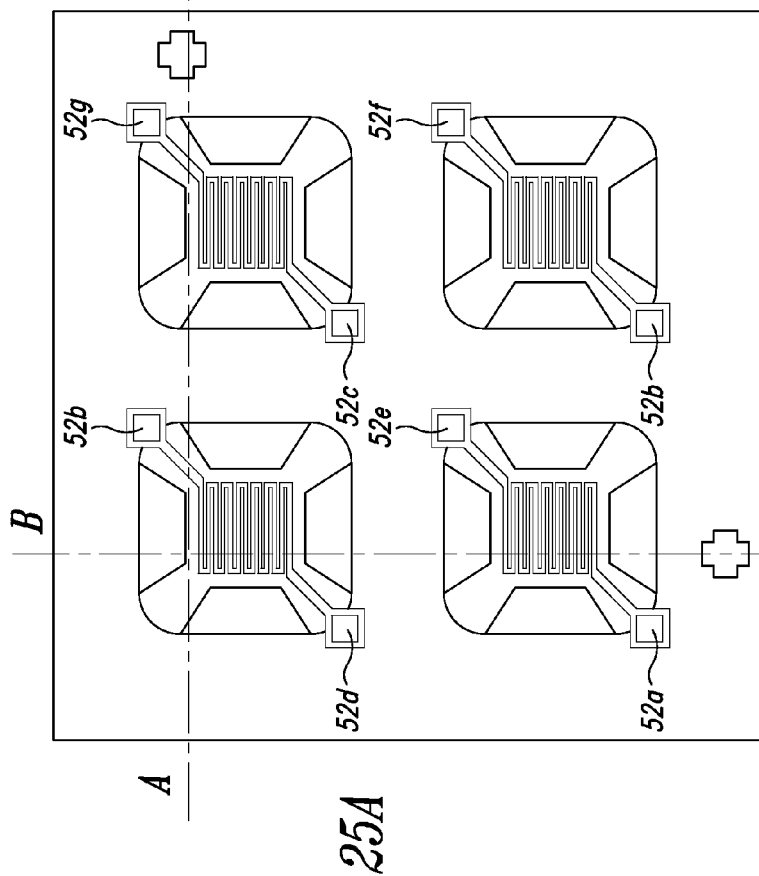
Figure 25B:
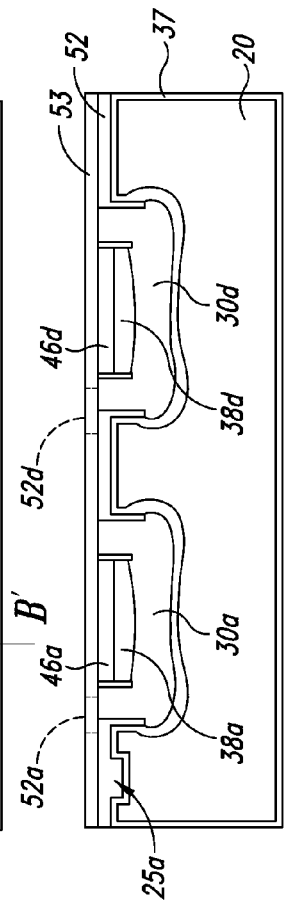

Then, a fifth photolithography step follows useful to open the electric contacts of the heating elements through the layer 52. Therefore, it is carried out as shown respectively in FIGS. 25A-C. More in particular, by carrying out a spin coating step by using a photoresist layer with thickness higher than the difference of heights in the structure, we will have a planarization effect. Obviously, since the resist is liquid it will completely fill up the cavity underlying the suspended membrane (see FIG. 23/33). After the photo-sensitization of the resist the development will be carried out and then the part below the cavity being not impressed by the light will be removed by the solvents of the development step. The etching of the passivating layer will then follow and then the removal of the resist will have to be carried out taking care of concluding this step with a removal step in wet, so that all the possible resist residues are eliminated. The deposition of a fifth photoresist layer 53 on the dielectric layer 52 follows, leaving exposed the portions 52a-52h of the dielectric overhanging the squared, or of other shape, regions which will constitute the contacts of the heater 49a-49d and 51a-51d. After a chemical etching of the exposed portions 52a-52h of the dielectric layer 52, as shown in FIGS. 26A-C, and the removal of the photoresist layer 53, the openings 54a-54d and 55a-55d of the dielectric layer 52 remain respectively on the squared regions 49a-49d and 51a-51d. FIG. 26B shows in phantom lines a first and a fourth opening 54a and 54d of the dielectric layer 52 (in phantom lines because BB' does not cross the openings 54a, 54d); FIG. 26C shows in phantom lines a third opening 55c and the fourth opening 55d of the dielectric layer 52 (in phantom lines because AA' does not cross the portions 55c, 55d), a classical opening of contact openings on a poly layer.

Finally, as shown in FIGS. 27A-C, a barrier layer 56, for example TiTiONTi (Titanium/oxinitride of titanium/titanium) or other similar material, is deposited, through "sputtering", with the aim of avoiding that, during a successive metallization step of the contacts, the superficial metallic oxides constituting the sensitive element are diffused in the dielectric layer 52 due to the high temperature and for ensuring the mechanical adhesion between the metallic layer and the underlying insulating dielectric layer.

The method goes on, then, with the realization of the electrodes of the sensitive element of the gas sensor and of the electric contacts of the heating element. The electrodes are realized through a metallic layer which, is selectively grown by means of an electrodeposition process. In this case, in particular, on the barrier layer 56, a first metallic layer 57 is deposited, through "sputtering", having a thickness equal to some hundreds of Angstroms, which serves as "seed layer" for the growth of a thick metallic layer and whereon a successive electrodeposition step is carried out. This step is shown in FIGS. 28A-C. Moreover, the metallic layer 57, besides being a conductive material, should have the property of being inert when contacted by the sensitive element realized in successive steps for avoiding any contamination or poisoning of said layer. This metallic layer is, in fact, chosen in the group of the noble metals.

According to another embodiment, instead, this seed metallic layer 57 is deposited through "sputtering" and subsequently shaped through typical lithography and etching processes.

As shown in FIGS. 29A-C, a sixth photoresist layer 58 is subsequently deposited above the seed metallic layer 57, so as to leave exposed four other regions 59a-59d of comb-like shape, with interdigitated geometries, the two metallic branches whereon the sensitive element will be deposited are not directly connected to each other, they are the rheophores of a resistor whose resistive element is exclusively the metallic oxide which will constitute the sensitive element. In fact, each contact between the two rheophores (resistance almost void) being in parallel with the resistance offered by the sensitive element would nullify each detection effect, a gas or other organic substance being present. In theory, it would be enough to simply contact the metallic oxide layer with two simple metallic lines, the structure, comb-like, interdigitated or of any other shape, the non-contact between the two electrodes being assured, serves only to increase the contact area. Playing with this parameter and with the distance between the two electrodes, the thickness of the metallization, etc. we can realize the resistor of a desired value, knowing the intrinsic resistivity of the sensitive material in the absence of substances to be detected, which has a first end ending, through a first oblique arm 60a-60d, in a first squared region 61a -61d and a second end ending, through a second oblique arm 62a-62d, in a second squared region 63a-63d, with a complementary geometry to that of the heating elements, as it is clear from FIG. 29A.

Figure 31C:
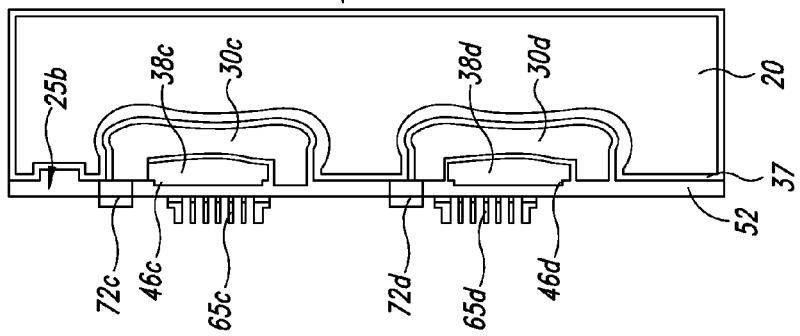
Figure 31A:
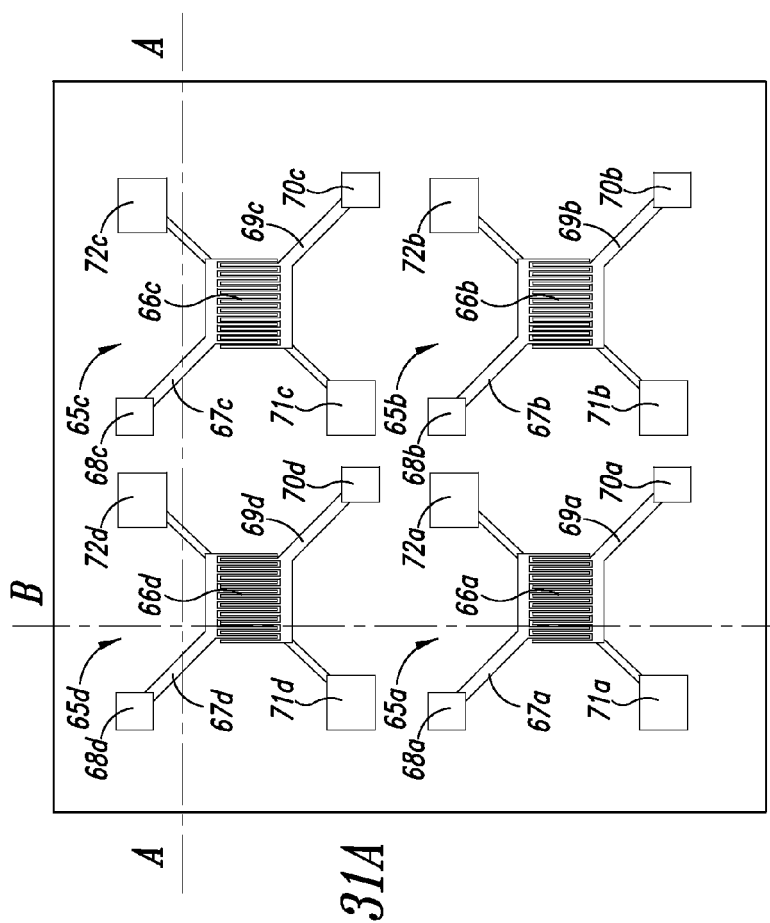
Figure 31B:
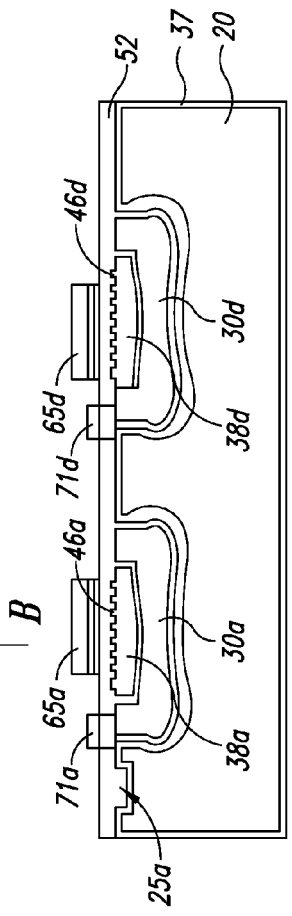

Subsequently, the step of electrodeposition is carried out, through which a second and thicker metallic layer 64 is grown, as shown in FIGS. 30A-C. The thickness of the metallic layer 64 increases proportionally to the duration of the electrodeposition process and, consequently, the series resistance of the electrodes decreases (for example from 0.4 micron to more than 10 micron). Moreover, the thickness of the metallic layer 64 is lower than the thickness of the photoresist layer 58, which allows to carry out a "lift-off" process, leaving, further to the removal of the photoresist layer 58, portions of metallic layer 64 on the interested areas defined through photolithography, as shown in FIGS. 31A-C. Moreover, the seed metallic layer 57 is removed and an etching of the barrier layer 56 is carried out. In this way, the electrodes 65a-65d are formed, comprising a portion of the barrier layer 56 and a portion of the second metallic layer 64. The electrodes 65a-65d have a geometry determined by the photolithography and, in particular, are constituted by a region 66a-66d with comb-like shape having a first end ending, through a first oblique arm 67a-67d, in a first squared region 68a-68d and a second end ending, through a second oblique arm 69a-69d, in a second squared region 70a-70d. In particular, FIG. 31B shows in phantom lines a first and a fourth electrode 65a and 65d; FIG. 31C shows in phantom lines a third electrode 65c and the fourth electrode 65d.

In this way, for each heating element, four pairs of electric contacts are also formed (71a,72a), (71b,72b), (71c,72c), (71d,72d), comprising portions of the barrier layer 56 and portions of the second metallic layer 64. In particular, FIG. 31B shows the first electric contacts 71a and 71d of a first and a fourth pair of electric contacts; FIG. 31C shows the second electric contacts 72c and 72d of a third pair and the fourth pair of electric contacts.

Figure 32C:
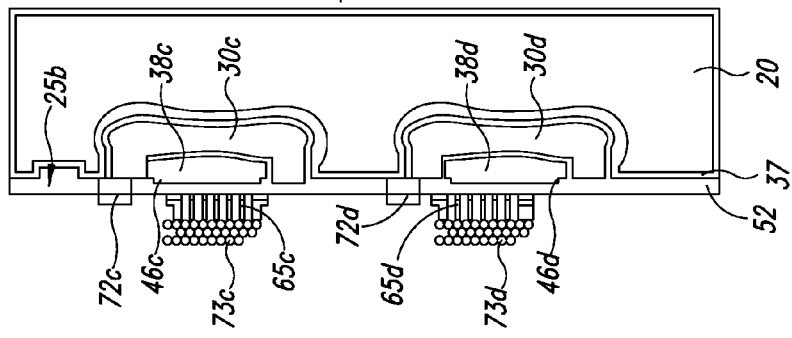
Figure 32A:
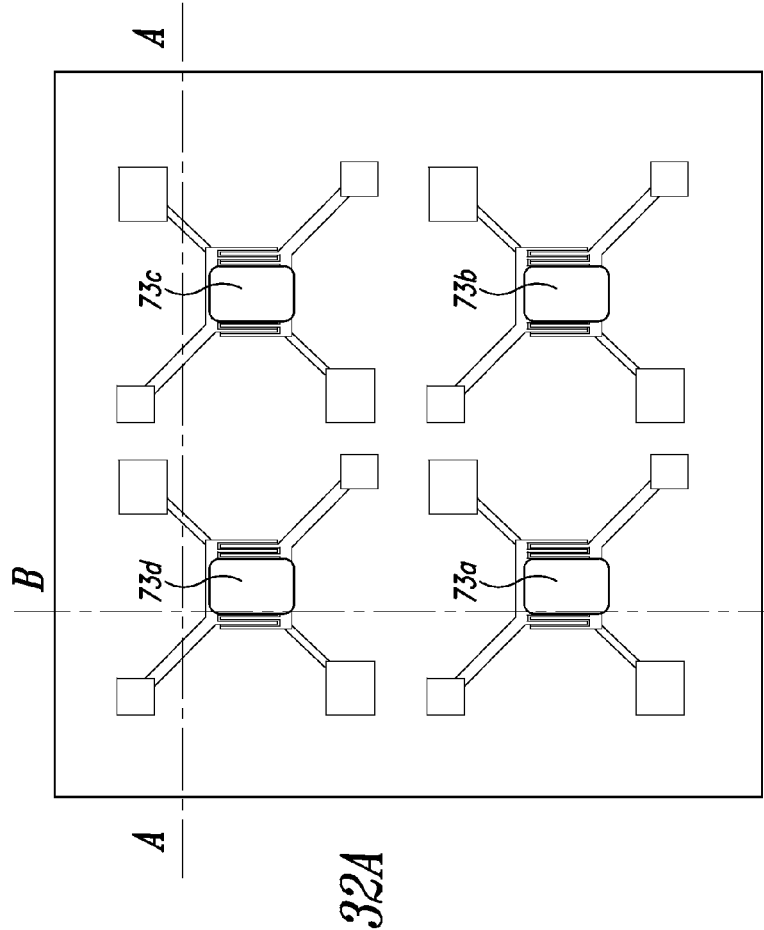
Figure 32B:
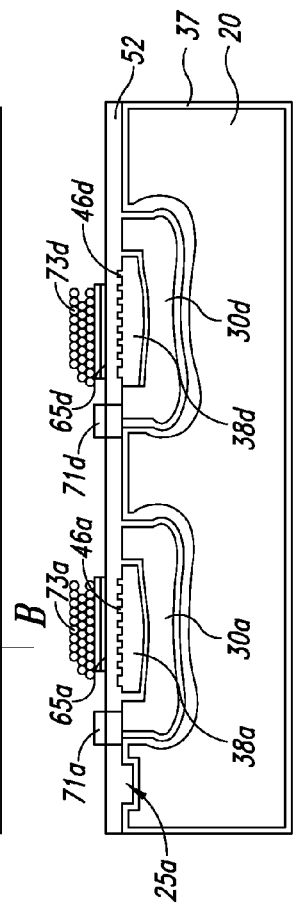

Subsequently, as shown in FIGS. 32A-C, on the electrodes 65a-65d sensitive elements 73a-73d are realized, formed by deposited sensitive metallic layers. Each sensitive metallic layer comprises a group of metallic oxides of different types and morphological characteristics, each of which is "functionalized", by chemistry or already in the synthesis phase, i.e., made more or less selective with respect to the volatile species which are absorbed. In particular, FIG. 32B shows the longitudinal sections of a first and of a fourth sensitive element 73a and 73d; FIG. 31C shows the cross sections of a third sensitive element 73c and the fourth sensitive element 73d.

The sensitive layer is prepared and dispensed with several techniques, for example "sol-gel", "inkjet printing", "screen printing", "microdispensing", according to what the application requires, either a thick sensitive layer, and, thus, more sensitive but slower in the response, or thin and faster. Moreover, the sensitive layer is dispensed selectively and exclusively above the electrodes, in the liquid form or, alternatively, gel or, alternatively, amalgam or, alternatively, paste. In any case, the solvent should be eliminated (and not the metallic oxide obviously). Moreover, generalizing the method to the manufacturing of more devices, all the metallic electrodes formed constitute an interconnected network of conductive paths which run inside the scribe lines of the devices. In consequence, when on the electrodes an external voltage, about double with respect to the operative voltage of the devices, is applied, all the heating elements present on the silicon wafer are connected in parallel and activated simultaneously. In this way, the temperature attained on the membranes is of about 700° C., and, maintaining this temperature for some minutes, the sensitive elements 73a-73d are thus subjected to the known sintering phenomenon which compacts the metallic oxides and increases their electric conductivity. After the deposition of the sensitive layer a sintering of the sensitive layer is necessary, which, according to the state of the art, is carried out through a thermal process in oven. Our idea is based on the fact that the sintering of the sensitive material can be directly carried out on wafer by using the same heaters of the various sensors, exploiting the high thermal and electric insulation offered by the suspended dielectric membrane realized as described above. With the aim of carrying out this process on a whole wafer, temporary electric connections will be provided, inside the scribe lines, these electric lines will connect the heaters of the devices exclusively while they are on the whole wafer. These dielectric buses will be all connected to each other with two or more main contacts on the wafer, after the cut all these lines will be eliminated and then each device will be independent from each other. This will allow to carry out the sintering of the sensitive material directly on the wafer, without any process in oven, after the deposition of the same material or even during this step by simply applying an electric voltage suitable inside the wafer.

Therefore, the method allows to obtain a "self curing" structure, i.e., capable of carrying out the sintering both during and after the dispensation of the material, for example through "ink jet", by simply connecting temporarily the silicon wafer with a voltage generator. Moreover, this thermal process is directly carried out on the silicon wafer, without the use of a stove or of an oven.

Figure 33C:
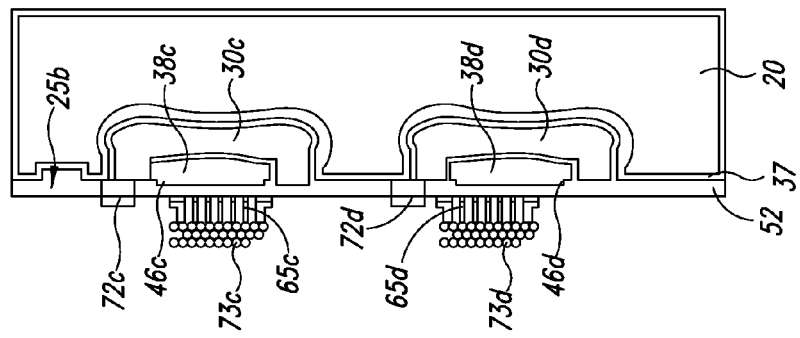
Figure 33A:
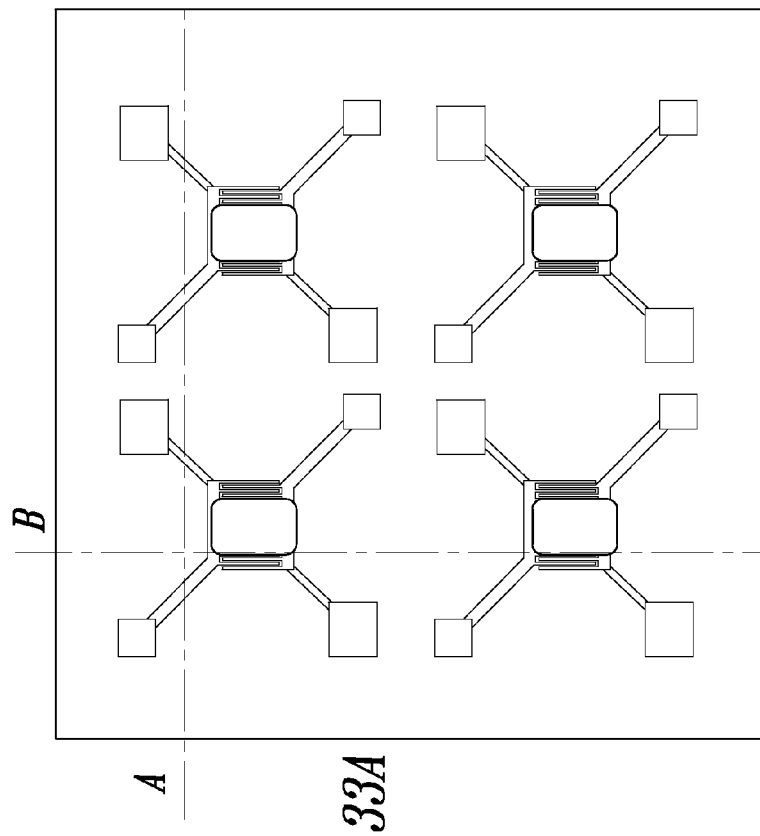
Figure 33B:
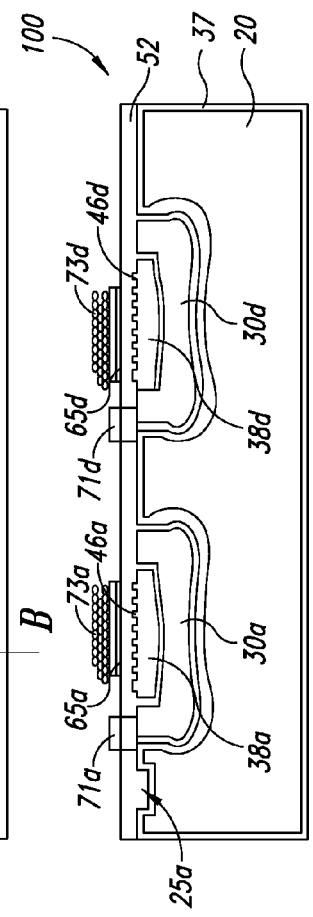
Figure 34:
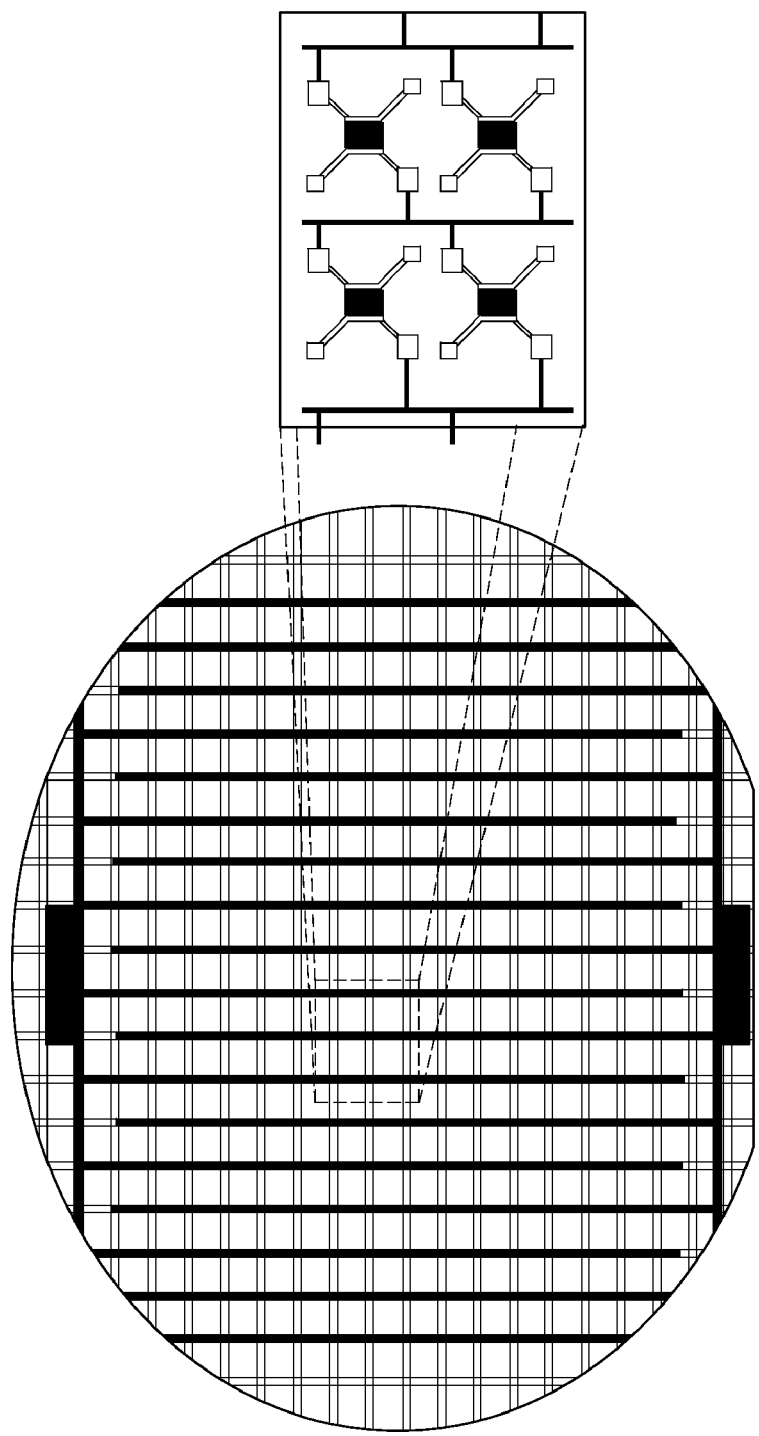
FIG. 34 shows a scheme of an example of the interconnections between the heating elements of the gas sensor, inside a single silicon wafer, determining a sintering process of the metallic oxides of the sensitive element, according to one embodiment.

FIGS. 33A-C shows the gas sensor 100, obtained after the "self curing" step, and FIG. 34 shows a scheme of the electric connections between the heating elements of the gas sensor, inside a single silicon wafer, which determine the sintering process of the metallic oxides. All the connections present on the silicon wafer are then automatically eliminated during the cut of the devices ensuring the electric independence of each single gas sensor present on the silicon wafer.

Figure 35:
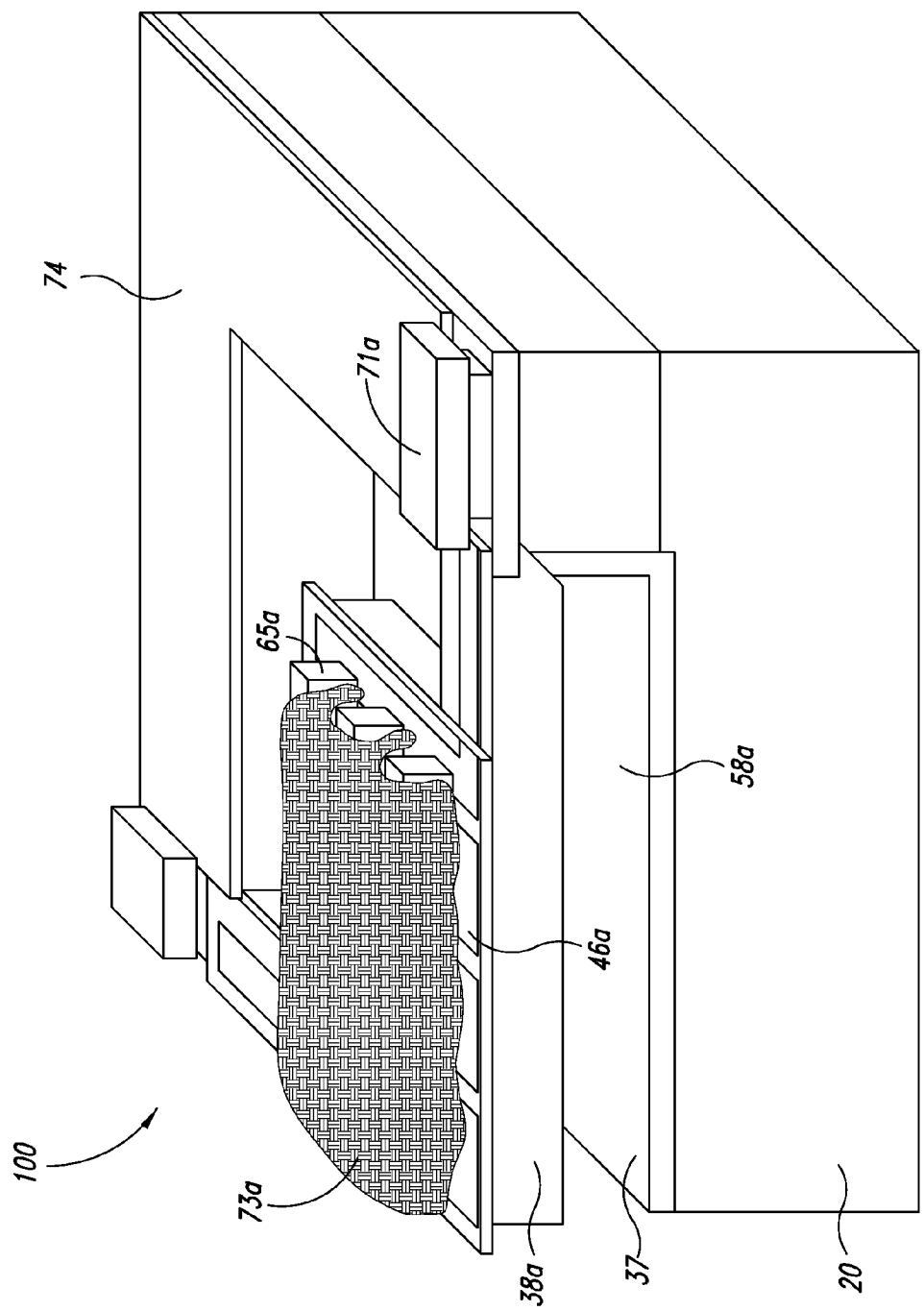
FIG. 35 shows a three-dimensional section view of a gas sensor realized with the method according to one embodiment.

By way of example, FIG. 35 shows a three-dimensional view of a portion of the gas sensor 100 realized with the method described herein, which also comprises a passivation layer 74. The passivation layer 74, has the function of electrically insulating the structure of the heater from that of the electrodes of the sensitive layer, but at the same time should not prevent its heat transfer.

Naturally, the area of the device, the geometry and the sizes of the membrane and of all the components of the gas sensor vary according to the type of application, of the operation conditions, of the temperature and of the thermal power of the device.

In conclusion, the method described herein allows to realize a low cost gas sensor that can be integrated on semiconductor substrates, with the standard technology of the electronic circuits.

In particular, the method allows to integrate a plurality of sensors, each one specific for a specific family of substances, in the same "chip". In this way, it is possible to realize an "electronic nose" useful for applications both in the chemical and biological field.

A further advantage of the method described consists in realizing, starting from a suspended crystalline structure whose thickness is of some microns and which is exposed to the environment from both faces, a suspended membrane completely formed by silicon oxide of thickness that can be obtained with difficulty through a superficial oxidation process. The anchorages of the suspended dielectric membrane to the sensor have the function of mechanical support also for the electric paths of the heater and of the sensor, starting from the connection contacts provided on the substrate up to the suspended electric membrane. Moreover, the sensor can be realized, together with the circuitry, both from the front and from the back of the silicon wafer, thus reducing the area occupation on the "chip" and increasing the mechanical strength of the device.

The method described herein, moreover, be used for all the applications in which it is necessary to carry out a heating, also at high temperature, of a limited and selected area of the "chip".

Finally, a further advantage of the method described is represented in that the use of the "inkjet" and "screen printing" techniques for depositing the sensitive layer allows to use a different sensitive material for each device, thus allowing to simultaneously detect different substances.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method, comprising:
    manufacturing a gas sensor integrated on a semiconductor substrate, the manufacturing including:
        realizing a first plurality of openings in said semiconductor substrate;
        realizing a crystalline silicon membrane suspended on said semiconductor substrate, thereby forming an insulating cavity buried in said substrate;
        realizing a second plurality of openings in said semiconductor substrate and extending to the insulating cavity;
        realizing, through a thermal oxidation process of said suspended crystalline silicon membrane, a suspended dielectric membrane;
        realizing, through selective photolithography, a heating element;
        realizing, through selective photolithography, an electrode and a pair of electric contacts of the heating element; and
        selectively realizing, above said electrode, a sensitive element, the selectively realizing including compacting layers of metallic oxide through a sintering process generated in said gas sensor by connecting said electrode to a voltage.

2. The method of claim 1 wherein said step of realizing a first plurality of openings in said semiconductor substrate is preceded by realizing, in said semiconductor substrate, a reference opening by:
    forming a masking dielectric layer on said substrate;
    depositing a first photoresist layer on said masking dielectric layer, leaving exposed a portion the masking dielectric layer overhanging a portion of said substrate;
    carrying out a chemical etching of said masking dielectric layer;
    removing said first photoresist layer;
    carrying out a chemical etching of said substrate; and
    removing said masking dielectric layer.

3. The method of claim 1, wherein realizing said first plurality of openings in said semiconductor substrate comprises:
    depositing a dielectric layer;
    depositing a photoresist layer on said dielectric layer leaving portions of the dielectric layer exposed through a plurality of spaced openings, the spaced openings forming a region of polygonal shape;
    carrying out a chemical etching of said dielectric layer;
    removing said photoresist layer; and
    carrying out a chemical etching of said substrate using the dielectric layer as a mask.

4. The method of claim 1, wherein realizing said crystalline silicon membrane suspended on said semiconductor substrate comprises:

removing said dielectric layer;
carrying out a thermal process, with hydrogen at a temperature comprised between 1000° C. and 1300° C.

5. The method of claim 4, wherein said carrying out the thermal process superficially closes said plurality of openings with foils of crystalline silicon, forming at the same time said insulating cavity buried in said substrate.

6. The method of claim 5, wherein said foils of crystalline silicon are anchored to said substrate peripherally and through thin structures of crystalline silicon arranged between said insulating cavity and additional insulating cavities.

7. The method of claim 1, wherein realizing said second plurality of openings in said semiconductor substrate comprises:
depositing, on said crystalline silicon membrane, a masking dielectric layer;
depositing, on said masking dielectric layer, a photoresist layer, leaving exposed a plurality of polygonal regions of the masking dielectric layer in correspondence with said insulating cavity;
carrying out a chemical etching of said masking dielectric layer;
removing said photoresist layer;
carrying out a chemical etching of said substrate;
removing said masking dielectric layer.

8. The method of claim 7, wherein said polygonal regions are trapezoidal.

9. The method of claim 1, wherein realizing said suspended dielectric membrane comprises carrying out said thermal oxidation process at a temperature comprised between 800° C. and 1300° C. in atmosphere containing oxygen, depositing and growing a layer of thermal oxide on said suspended crystalline silicon membrane.

10. The method of claim 1, wherein realizing said heating element comprises:
depositing a layer of conductive material above said suspended dielectric membrane;
depositing a layer of photoresist on said layer of conductive material, leaving exposed, in correspondence with said suspended dielectric membrane, a region with coil-like shape having a first end ending, through a first oblique arm, in a first squared region and a second end ending, through a second oblique arm, in a second squared region;
carrying out a chemical etching of said layer of conductive material; and
removing said layer of photoresist.

11. The method of claim 10, wherein depositing said layer of conductive material includes depositing polysilicon and doping the polysilicon in situ during the depositing.

12. The method of claim 1, wherein said heating element comprises a region of coil-like shape having a first end ending, through a first oblique arm, in a first squared region and a second end ending, through a second oblique arm, in a second squared region.

13. The method of claim 12, wherein realizing said electrode and said pair of electric contacts is preceded by:
depositing a passivating thin dielectric layer;
depositing a first photoresist layer on said thin dielectric layer, leaving exposed a plurality of portions of the thin dielectric layer overhanging respectively said first squared region and said second squared region;
carrying out a chemical etching of said exposed plurality of portions of said thin dielectric layer, thereby creating a first opening and a second opening in the thin dielectric layer respectively above said first squared region and said second squared region;
removing said first photoresist layer; and
depositing a barrier layer on the thin dielectric layer and in the first and second openings.

14. The method of claim 13, wherein said barrier layer is deposited through sputtering of a TiTiONTi material to avoid diffusion and to ensure adhesion.

15. The method according to claim 13, wherein realizing said electrode and said pair of electric contacts comprises:
depositing, on said barrier layer, a seed metallic layer;
depositing a second photoresist layer on said seed metallic layer, leaving exposed the region of coil-like shape;
growing, through electrodeposition from said seed metallic layer, a thick metallic layer;
removing said photoresist layer;
removing said seed metallic layer;
carrying out a chemical etching of said barrier layer.

16. The method of claim 1, wherein said electrode comprises a region of coil-like shape having a first end ending, through a first oblique arm, in a first squared region and a second end ending, through a second oblique arm, in a second squared region.

17. The method of claim 1 wherein connecting said electrode to the voltage includes connecting in parallel of a plurality of heating elements comprised in a matrix of gas sensors integrated on said substrate.

18. A method, comprising:
manufacturing a gas sensor integrated on a semiconductor substrate, the manufacturing including:
realizing a crystalline silicon membrane suspended on said semiconductor substrate, thereby forming an insulating cavity buried in said substrate;
realizing, through a thermal oxidation process of said suspended crystalline silicon membrane, a suspended dielectric membrane; and
realizing, above said suspended dielectric membrane, a sensitive element
realizing, above said suspended dielectric membrane, a heating element; and
realizing an electrode and a pair of electric contacts of the heating element, wherein the sensitive element is realized above the electrode.

19. The method of claim 18, wherein realizing the sensitive element includes compacting layers of metallic oxide through a sintering process generated in said gas sensor by connecting said electrode to a voltage.

* * * * *